United States Patent
Dennin et al.

(10) Patent No.: US 9,494,505 B2
(45) Date of Patent: Nov. 15, 2016

(54) SCANNING NON-CONTACT SURFACE MICRORHEOMETER

(71) Applicant: The Regents of the University of California, Oakland, CA (US)

(72) Inventors: Michael Dennin, Irvine, CA (US); Thomas Boatwright, Fremont, CA (US); Alexander Levine, Los Angeles, CA (US); Arthur A. Evans, Culver City, CA (US); Roy Shlomovitz, Afula (IL)

(73) Assignee: The Regents of the University of California, Oakland, CA (US)

( * ) Notice: Subject to any disclaimer, the term of this patent is extended or adjusted under 35 U.S.C. 154(b) by 226 days.

(21) Appl. No.: 14/065,755

(22) Filed: Oct. 29, 2013

(65) Prior Publication Data
US 2014/0150534 A1    Jun. 5, 2014

Related U.S. Application Data

(60) Provisional application No. 61/719,905, filed on Oct. 29, 2012.

(51) Int. Cl.
*G01N 11/00*    (2006.01)
*G01N 13/00*    (2006.01)

(52) U.S. Cl.
CPC .............. *G01N 11/00* (2013.01); *G01N 13/00* (2013.01); *G01N 2203/005* (2013.01); *G01N 2203/0089* (2013.01); *G01N 2203/0286* (2013.01)

(58) Field of Classification Search
CPC ............ G01N 2203/0094; G01N 2015/1415; G01N 2013/0233; G01N 2015/1062; G01N 2015/105

USPC ........................ 73/54.01, 579, 861.95, 54.23
See application file for complete search history.

(56) References Cited

U.S. PATENT DOCUMENTS

| | | | | |
|---|---|---|---|---|
| 6,991,939 B2 * | 1/2006 | Walt | ...................... | G21K 1/006 250/251 |
| 7,305,319 B2 * | 12/2007 | Vicci | ...................... | G01Q 10/06 702/152 |
| 7,745,788 B2 * | 6/2010 | Appleyard | ............. | G21K 1/006 204/478 |
| 2008/0310009 A1 * | 12/2008 | Liao | ................... | G01N 15/1475 359/305 |

FOREIGN PATENT DOCUMENTS

| | | | | |
|---|---|---|---|---|
| CN | 102519862 A | * | 6/2012 | ............ G01M 10/00 |
| WO | WO 2012112977 A1 | * | 8/2012 | ......... G01N 21/4795 |

OTHER PUBLICATIONS

Neuman KC, Block SM. Optical trapping. The Review of scientific instruments. 2004;75(9):2787-2809. doi:10.1063/1.1785844.*

* cited by examiner

*Primary Examiner* — Laura Martin
*Assistant Examiner* — Jean Morello
(74) *Attorney, Agent, or Firm* — Joseph R. Baker, Jr.; Gavrilovich, Dodd & Lindsey LLP

(57) ABSTRACT

The disclosure provides non-contact microrheological methods that can measure the fluctuation of a particle in a monolayer, where the particle is hydrodynamically coupled to the monolayer. The disclosure further comprises devices to carry out the non-contact microrheological methods thereof, including Laser Tweezer devices which can study in vitro biological processes.

8 Claims, 10 Drawing Sheets

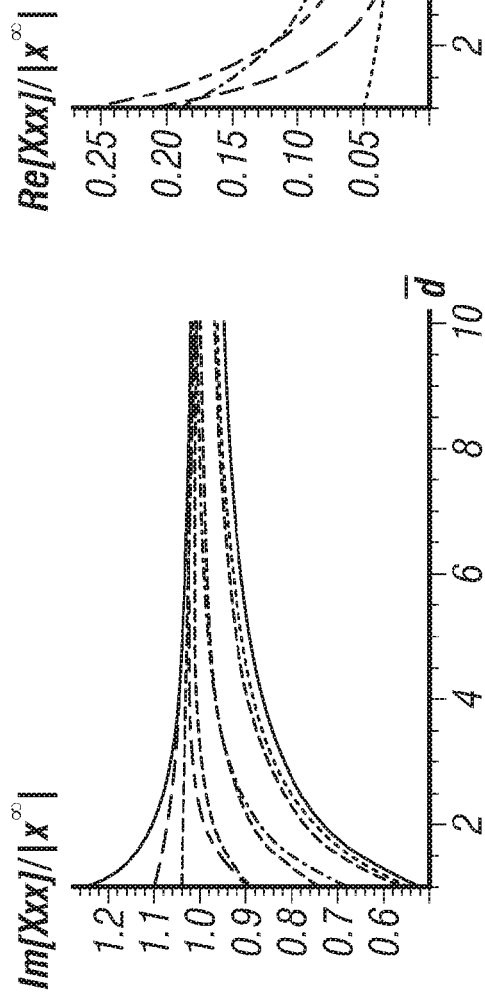
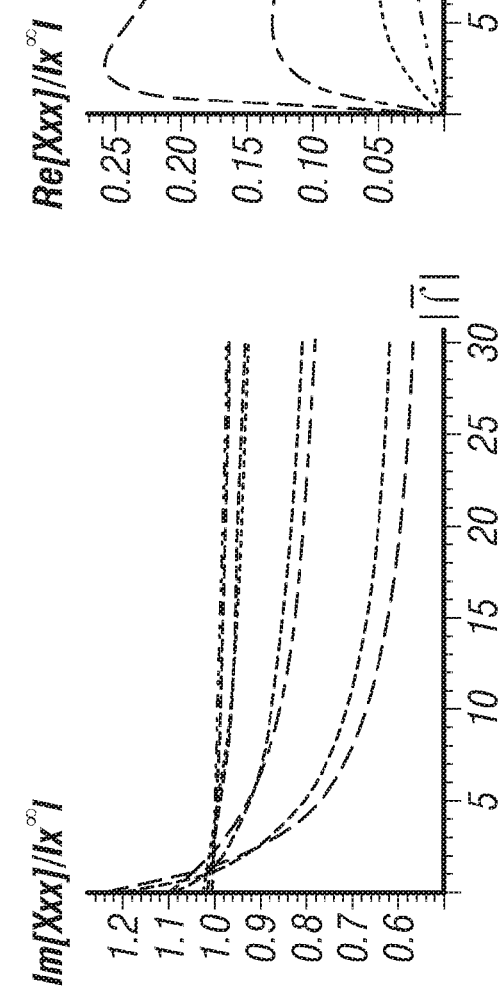
FIG. 2A
FIG. 2B
FIG. 2C
FIG. 2D

SCANNING NON-CONTACT SURFACE MICRORHEOMETER

CROSS REFERENCE TO RELATED APPLICATIONS

This application claims priority under 35 U.S.C. §119 from Provisional Application Ser. No. 61/719,905, filed Oct. 29, 2012, the disclosure of which is incorporated herein by reference.

GOVERNMENT LICENSE RIGHTS

This invention was made with Government support under Grant No. DMR-0907470 awarded by the National Science Foundation. The Government has certain rights in this invention.

TECHNICAL FIELD

The disclosure provides a non-contact mode for determining surface fluidity and elasticity.

BACKGROUND

Understanding the molecular basis for a wide-range of biological processes has been a major success of the direct application of chemical techniques to biological problems. More recently, the awareness of the importance of the mechanical properties of living cells and their mechanical interaction with the extra-cellular environment is rapidly growing in the biological community. It is now clear that cells partake in a sensitive force balance, maintenance of which is a key factor to normal cellular function. For example, it has been observed that cellular proliferation and survival is optimal when culture substrates match their natural in-vivo stiffness. In the area of stem cell biology, researchers have discovered strong correlations between extra-cellular matrix (ECM) stiffness and stem cell lineage. For many cells types, including tumor cells, cells have been shown to generate compensatory forces in response to external loads or matrix stiffness increases in a process called mechanoreciprocity.

Such evidence supports hypotheses in which upsetting the force balance can have a significant impact on cellular behavior in cancer related processes. For example, pressure was shown to upregulate the Src-PI3K-FAK-Akt signaling pathway, which increases cell membrane-ECM adhesion in tumor cells. Tumor progression in vivo and in 3D mammary epithelial cell (MEC) culture correlated with increased ECM crosslinking and stiffness.

For instance, the plasma membrane is mechanically coupled to the inside of cell, where it interacts with the dynamic actin cytoskeleton, and not surprisingly, it has been shown that cytoskeleton rearrangement can have profound effects on plasma membrane deformability, tension, and fluidity. Also, the plasma membrane is mechanically coupled to the ECM on the outside of the cell through receptors including the integrin family transmembrane adhesion molecules. Membrane fluidity and curvature plays a direct role in facilitating clustering of these proteins, which initiates mechano-signaling to promote differentiation, proliferation and invasion. Additionally, lipid rafts, a component of the plasma membrane that is associated with a mechanical response, can modulate local membrane stiffness. These examples not only involve the interface, but also rely on fundamentally active processes driving the system out of equilibrium. This represents a small subset of roles and effectors of membrane stiffness, both known and yet to be discovered. The search for new roles and effectors should be carried out in a natural 3D context.

Most methods attempt to use micron scale particles placed in the interface and measure their fluctuations. This does not really solve the problem as the particles have too much contact with the fluid on either side of the interface (being much larger than the molecular layer of interest) and they disturb the layer, changing its properties. Both of these are major disadvantages that needed to be overcome.

SUMMARY

The disclosure provides for a non-contact microrheological method comprising: measuring the fluctuation of a particle in a monolayer by using a weak laser trap in combination with a back focal plane displacement detection scheme, wherein the particle is held at a fixed depth below an air/liquid, liquid/liquid, or solid/liquid interface and its small fluctuations in a plane parallel to the monolayer surface is measured, and wherein the particle is hydrodynamically coupled to the monolayer. In a certain embodiment, a non-contact microrheological method disclosed herein uses a quadrant photodiode detection system to measure a particle's position in a monolayer. In another embodiment a non-contact microrheological method disclosed herein, comprises extracting from the particle fluctuation measurements the in-plane response function. In yet another embodiment, a non-contact microrheological method disclosed herein, comprises determining the response function in terms of the hydrodynamic modes of the system and their associated moduli, such as the response function taking into account the role of the subphase, the contact angle between the particle and the interface, and changes in the monolayer itself induced by the particles.

In a certain embodiment, the disclosure further provides for correcting particle fluctuation measurements for one or more optical effects resulting from using a non-contact microrheological method disclosed herein, including (1) changes in the background intensity of reflected light as the depth is changed, (2) particle lensing effects acting on reflected light, or (3) a combination thereof. In yet another embodiment, the disclosure also provides for a non-contact microrheological method disclosed herein, which utilizes one or more of Equations 1-20 disclosed herein.

In a particular embodiment, the disclosure provides for a device for carrying out a non-contact microrheological method disclosed herein. In a further embodiment the device comprises an existing Langmuir monolayer trough coupled with a 100× water immersion objective; an optical trap using a 1064 nm Nd:YVO4 laser; an optical system comprising a beam expander, steering lenses, mirrors, and water immersion objective, which focuses the beam to form the optical trap, wherein the trough is attached to a vertical translation stage so that the fixed objective can trap particles at various distances below the surface. In yet a further embodiment, a device for carrying out a non-contact microrheological method disclosed herein, comprises the device depicted in FIG. 4. In yet a further embodiment, a device for carrying out a non-contact microrheological method disclosed herein, comprises the laser tweezer device depicted in FIG. 12, wherein the laser tweezer device can measure bulk mechanical properties of biological systems. In another embodiment, a laser tweezer device disclosed herein comprise using SPIM based microrheological methods, and wherein the device uses a response function that is measured directly by comparing an applied force and the particles displacement using an oscillatory measurement ("AMR").

DESCRIPTION OF DRAWINGS

FIG. 2A-D provides the imaginary and real plots of interface fluctuations. The imaginary (A) and real (B) parts of the normalized tracer susceptibility X for forces parallel to the interface as a function of the normalized distance $\bar{d}$ for various values of the modulus of the SD length $|\bar{l}|$=0, 1, 3, 10, 100, ∞ (black, blue, purple, orange, gray). The phases are chosen to correspond to purely elastic (solid lines) and viscous (dashed lines) monolayers. The imaginary (C) and real (D) parts of as a function of χ for various depths below the monolayer: $\bar{d}$=1, 2, 5, 10 (blue, purple, yellow, green). The imaginary part decreases as the surface modulus increases and the variation with $|\bar{l}|$ is greater for shallower depths. If, $|\bar{l}|<|l|_c \approx 5$ the susceptibility close to the surface is higher than the Stokes value (infinite depth).

DETAILED DESCRIPTION

Figure 1:
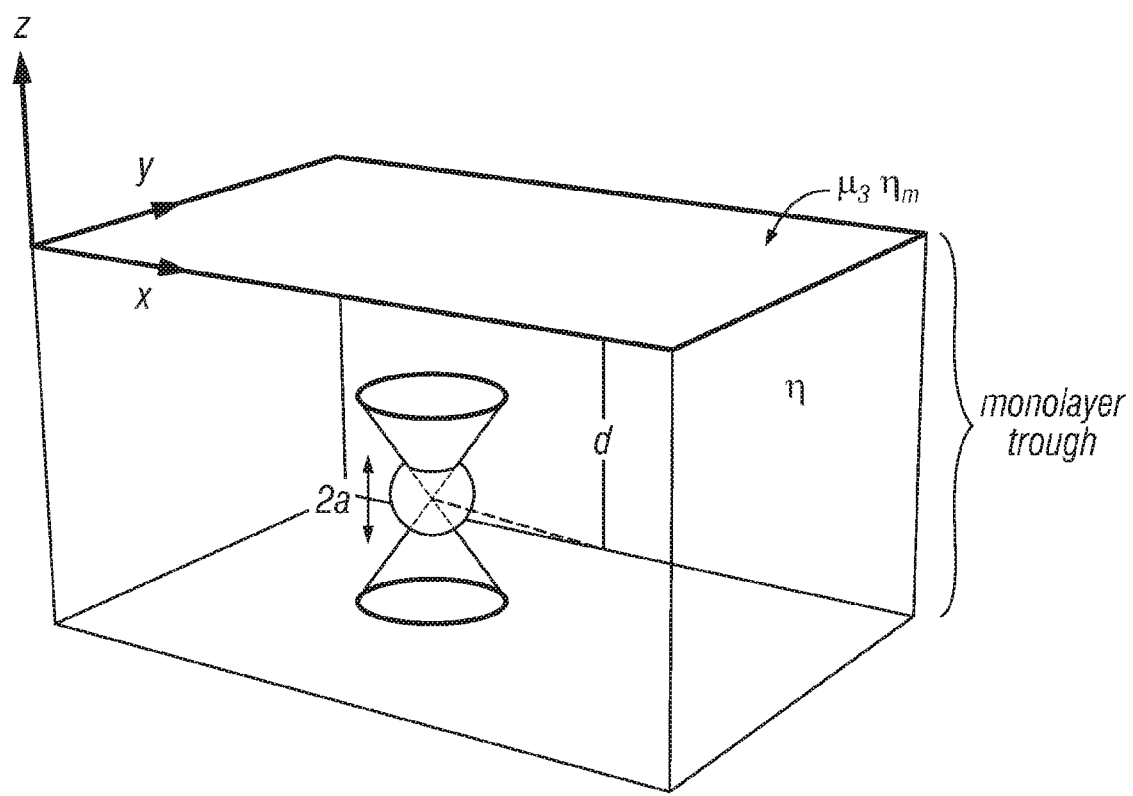
FIG. 1 presents a schematic for the proposed non-contact microrheological probe. A diagnostic particle of radius a is submerged at depth d beneath the monolayer, and its fluctuation spectrum is measured with the assistance of an optical tweezer trap.

As used herein and in the appended claims, the singular forms "a," "and," and "the" include plural referents unless the context clearly dictates otherwise. Thus, for example, reference to "a probe" includes a plurality of such probes and reference to "optical tweezer" includes reference to one or more optical tweezers and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

The disclosure provides microrheological methods that can be used in devices for determining the bulk mechanical properties of biological systems. Microrheology utilizes the response of small probe particles to either thermal fluctuations or induced fluctuations, usually through magnetic or optical tweezers, to determine the visco-elastic properties of the surrounding medium. Understanding the molecular basis for a wide-range of biological processes has been a major success of the direct application of chemical techniques to biological problems. More recently, the awareness of the importance of the mechanical properties of living cells and their mechanical interaction with the extra-cellular environment is rapidly growing in the biological community. The underlying biophysics of cell mechanical integrity, motility, and the transduction of external mechanical stress into a biochemical response is now seen as central to biological processes such as cell adhesion and migration (e.g. durotaxis). A more complete appreciation for the role of mechanics in these processes will eventually impact clinical research in wound healing and the control of metastatic cancers. The basic element in the study of mechanics is the ability to measure stress-strain relations (the equivalent of force-displacement curves), e.g. the viscoelastic properties of materials. For biological systems, the details of the environment are integral to the mechanical properties of interest, so one cannot simply take purified material and place it in a conventional rheometer. The development of an instrument that can measure the mechanical properties of biological systems in vivo would be a truly transformative technology.

Interfaces in biological systems occur in a number of different places, including the cell membrane, membranes of organelles, and the air-water interface in lung alveoli. The interaction of the cytoskeleton with the cell membrane and the dynamical response of the lung surfactant layer at the air-water interface in alveoli provide two excellent examples of the importance of interfacial mechanical responses. The cytoskeleton is a chemically heterogeneous filamentous semi-flexible network that pervades the cytosol (cellular interior), and is cross-linked by a plethora of proteins, including molecular motors. A key feature of this system is the interactions between this polymer gel and cellular membranes. These interactions are responsible for the cell's ability to change shape, measure the elastic properties of the surrounding extra-cellular matrix, measure imposed stresses, and exert the forces necessary for movement. Therefore, to fully understand this system, the mechanical properties of the membranes need to be measured under the correct in vivo dynamical conditions. Lung-surfactant is a single layer of surface-active molecules that coat the interface between the air in the alveoli and the interstitial fluid. During the breathing cycle, this surfactant layer is highly deformed, as it is compressed and expanded. Its mechanical properties are critical for determining the response to this rapid and highly non-linear deformation. An open question in this system is the role of phase separation that generates structures on the 10's to 100's micron scale.

For research on the role of mechanics in cell membrane-ECM interactions to progress, there is a clear need for instrumentation that quantitatively measures the ECM mechanics at the interface between the cell and the ECM. Such measurements are essential for investigating how mechanical information is transmitted from the ECM to the cell through the interface formed by the cell membrane. The disclosure provides a method and device for carrying out Submerged probe interfacial microrheology (SPIM), which overcomes existing limitations of current technology and can transform the ability to quantitatively measure the impact of mechanical changes in the ECM and the cell membrane on various diseases, including cancer.

The characterization of interfacial mechanical properties remains an important experimental challenge with a wide range of applications. There are two distinct experimental environments in which interfacial measurements are of interest: air/water interfaces and fluid/fluid interfaces. The former is typically found in the study of Langmuir monolayers, two-dimensional layers of molecules at the air/water interface, while the latter is of interest in biological systems in which lipid bilayers are common as part of the cell membrane and intracellular structures.

Langmuir monolayers are relevant in a number of technological applications and as model systems for a range of biological problems and general studies of two-dimensional phase behavior. While there is a long history of macroscopic measurements of their mechanical properties, these techniques are difficult to adapt to in-situ measurements in biological systems and often do not provide critical information about local properties in highly heterogeneous systems. Consequently, there has been a long felt need in the art for methods which provide interfacial microrheological measurements that rectify the limitations and artifacts provided by the current methods.

Microrheology is a method that uses the observed displacement fluctuations (Brownian motion) of microscopic probes to extract that medium's rheological properties, by applying a fluctuation dissipation theorem. From that result, the observed fluctuation spectrum reports on the frequency-dependent response function of that particle to an applied force. A further step in the analysis requires one to determine that response function in terms of the hydrodynamic modes of the system (in the generalized sense) and their associated moduli. The principal advantages of using this indirect rheological measurement stem from the fact that the technique does not require the active deformation of large bulk samples of the material and by using only thermal forces it can be applied to the most fragile of structures. These properties make microrheology useful in the study of biopolymer networks in vivo and in situ in living cells. It also allows one to probe the rheology of fragile structures that have no three-dimensional realization—Langmuir monolayers and lipid membranes—since one does not have to couple the system to a macroscopic rheometer. Interfaces have also been studied with related techniques at liquid solid interfaces, measuring the effect of surface properties on diffusion. The central challenge for these microrheological studies of lower dimensional, e.g., interfacial systems, is the development of the necessary theoretical framework to compute the response function of a particle attached to the monolayer.

Langmuir monolayers, formed by the aggregation of surfactants at an air-water interface, have long served as a testing ground for exploring broken symmetry phases in low dimensional systems. They also serve as a model for biological membranes: a lipid monolayer in a Langmuir trough allows for precise chemical control and experimental access to a mimic of one leaflet of a cell membrane. In both cases, rheological probes can provide essential data on the low energy excitations of such complex phases and their moduli, as well as measurements of relevance to biomechanics at the cellular level. These rheological measurements, however, have proven to be problematic. Two main approaches have been employed: macrorheology using, for example, oscillatory rheometers, and microrheology using particle tracking. The former has difficulties measuring very fragile or compliant surface phases, and may, due to the macroscopic deformations imposed, access the nonlinear response regime. In light of these difficulties, the latter microrheological approach seems promising, but currently suffers from a "missing modulus" problem: when both macro- and microrheological approaches are compared, the microrheological data reports moduli up to four orders of magnitude lower.

Two potential causes for these large discrepancies are the uncertainty in tracer positioning and the unknown nature of boundary conditions between the particle and the monolayer. The interpretation of the particle tracking microrheology is based on the assumption that the tracer is embedded in the monolayer, but this is difficult to guarantee since it is difficult to resolve the vertical position of the tracer with sub-micron precision; moreover, higher surface pressures or more elastic monolayers may drive the tracer into the subphase. Even if the particle is embedded in the monolayer, its presence may locally disrupt the monolayer's structure—an effect seen in three dimensional microrheology necessitating more difficult two-particle approaches. These approaches are complicated by the role of a three-phase contact line at the particle and the lack of understanding of local structural perturbation of the monolayer caused by the presence of the particle.

Though proven methods exist for performing rheological measurements at interfaces, they are focused on macroscopic measurements (length scales of cm's or greater), generally designed for the air-water interface, and work best for relatively stiff system. In contrast, efforts to apply microrheology directly to interfaces using embedded particles or structures within the interface have achieved limited success, often disagreeing with macroscopic measurements by orders of magnitude. Given the clear need for local measurements of interfacial mechanical properties and the severe limitations of existing techniques, the disclosure provides devices that utilize non-contact microrheological methods disclosed herein which are capable of measuring the mechanical properties of biological interfaces in a wide-range of in-vivo situations. The devices and microrheological methods disclosed herein enable the research of a broad range of biological systems that were heretofore could not be properly analyzed.

Microrheology is an important and now widely used probe of soft materials. Essentially, it involves the determination of mechanical properties from the observation of stochastic trajectories of tracer particles via a generalized Stokes-Einstein relation. The technique's importance as a complement to, and extension of traditional rheological measurements arises from three fundamental strengths. It can easily probe a much wider frequency range than traditional, macroscopic rheology, currently between 0.1 Hz to 100 kHz. It can be used in microscopic samples and samples that cannot be studied in a traditional rheometer, such as biological cells. Since passive microrheology uses only thermally generated forces to move the probe, it can non-destructively measure the linear response of fragile or highly non-linear materials. Finally, because it is a local measurement of the rheology, it can detect heterogeneities that bulk rheology averages over.

Microrheology focuses on the frequency dependent complex shear modulus of a material, $G^*(\omega)$. In a frequency dependent measurement, $G^*$ connects the measured stress, $\sigma$, to an applied strain, $\gamma$: $\sigma(\omega)=G^*(\omega)\gamma(\omega)$. $G^*$ is determined by measurements of the linear response function $\chi(\omega)$ that connects the thermodynamically conjugate variables of force, $F(\omega)$, and displacement, $u(\omega)$: $u(\omega)=\chi(\omega)F(\omega)$. In the simplest cases, the generalized Stokes-Einstein relation for a particle of radius a is used to connect $G^*(\omega)$ and $\chi(\omega)$: $G^*=1/6a\chi(\omega)$.

There are two distinct microrheology approaches to measuring $\chi(\omega)$. For passive microrheology ("PMR"), the fundamental principle is the Fluctuation-Dissipation Theorem (FDT), linking observed equilibrium fluctuations of a variable (typically the translational degrees of freedom of the embedded tracer particle) to the dissipative part of $\chi(\omega)$. Specifically, if one were to measure the displacement fluctuations u(t) of a tracer then compute their power spectrum $\langle |u(\omega)|^2 \rangle$, this equilibrium measurement actually measures the imaginary (or dissipative) part of $\chi(\omega)$ of that tracer to an externally applied force through the FDT:

$$\langle |u(\omega)|^2 \rangle = \frac{2k_BT}{\omega}\mathrm{Im}[\chi(\omega)] \qquad (1)$$

The real (in phase) part can be then determined using Kramers Kronig relations (enforcing the causal nature of the response function). A primary advantage of PMR is that it does not require any calibration of an applied force, and by definition, the forces are linear. This allows for measurements of extremely fragile systems. A challenge is obtaining enough data for accurate application of the Kramers Kronig relations. Alternatively, the response function is measured directly by comparing an applied force and the tracer's displacement using an oscillatory measurement, e.g. active microrheology ("AMR"). Here, the challenge is applying a calibrated force, which is generally achieved through either optical or magnetic tweezers.

For either AMR or PMR, the theoretical challenge presented by microrheology is in the interpretation of the measured response function $\chi(\omega)$ in terms of the complex viscoelastic moduli $G^*(\omega)$ of the surrounding medium. Detailed calculations exist for three-dimensional, two-component, complex liquids and for two-dimensional viscoelastic monolayers, interfaces, and vesicles and even porous, viscoelastic shells. Additionally, calculations for viscoelastic thin-films, such as surfactant-actin complexes, exist. However, correctly using these calculations with realistic probe particles is one of the major challenges of applying microrheology to interfaces.

The interpretation of the response function for probe particles embedded in an interface is extremely sensitive to correctly accounting for the position of the particle relative to the interface for a number of reasons. Generally, one has to account for the three-phase contact line between the particle and the fluids both sides of the interface (note: one of these may be air). Additionally, there is the impact of the particle on the generally fragile interfacial structure. Finally, there is the experimental challenge of determining the exact location of the particle in the interface. The disclosure provides microrheological methods disclosed herein that can be used to probe interfacial rheology comprising using a response function near, but below, an interface.

The disclosure also provides microrheological methods disclosed herein that comprises tracking the fluctuations of two types of tracer-particle measurements. By tracking the correlated fluctuations of two distant tracer particles one can measure the rheological properties of the bulk material independently of the exact nature of the coupling of the tracer to its surrounding medium. The single-particle tracking experiments, however, are sensitive to the details of the coupling between the particle and the (possibly perturbed) medium. The disclosure further provides that by comparing the results of a single tracer-particle with microrheological methods that track two types of tracer-particles using a shell model one can examine in detail the nature of particle's interaction with the medium as shown in experiments provided herein.

As mentioned, a long-standing goal has been the development of local techniques for measuring the mechanical properties of Langmuir monolayers. Langmuir monolayers are monomolecular layers of insoluble, amphiphilic molecules that are confined to the air-water interface and exhibit a rich phase behavior. They are generally characterized by their surface pressure-area isotherms, defined as $\Pi = \gamma_w - \gamma$, where $\gamma_w$ is the surface tension of pure water and $\gamma$ is the surface tension of the water-monolayer system. Langmuir monolayers have been used extensively in modeling biological systems and provide a highly controlled environment. The rich phase behavior presents a wide-range of mechanical properties. In addition, measurements of these mechanical properties with macroscopic rheometers have a long history.

With Langmuir monolayers, one has easy access to the interface and the ability to engineer an arbitrarily complex fluid below the interface. By using model polymer systems attached to the Langmuir monolayer, one can model the visco-elastic bulk fluid of the cellular environment. Devices disclosed herein encompassing these systems are useful in approximating the full complexity of biological systems by using increasing complex steps.

In the Langmuir monolayer geometry, it is difficult to include cell cultures. Most of the techniques for measuring Langmuir monolayers rely on using structures inherent in the interfacial system, which are difficult to extend to biological systems, and have less than an order of magnitude of dynamic range. For particle based methods, one challenge is obtaining quantitative agreement between microrheology and macrorheology, though recent studies with magnetic disks are promising for stiff system. As discussed, lack of quantitative agreement is largely due to the challenge of understanding the appropriate theoretical framework for interpreting the microrheology results. The disclosure provides for devices comprising the non-contact microrheological methods disclosed herein which avoids these theoretical issues and is able to provide almost three orders of magnitude of dynamic range and perform measurements not possible with any existing technique.

The disclosure extends aspects of microrheology to the biological system of cells. As described below, a culture of Human Umbilical Vein Endothelial Cells (HUVEC) on glass was used in Experiments disclosed herein. A key feature of the HUVEC system is the ability to manipulate the properties of the cytoskeleton and the intra-cellular motor proteins responsible for force generation using standard bio-chemical techniques. Changes to the cytoskeleton are expected to impact the mechanical properties of the cellular membrane. The disclosure provides enabling in-vitro based Examples of the SPIM system of the disclosure with the HUVEC cells so as (1) to understand local unfolding dynamics of Langmuir monolayer systems; and (2) to impact of macroscopic deformations on the microscopic structure of an actin network associated with the air-water interface.

The analysis of submerged probe interfacial microrheology (SPIM) disclosed herein not only resolves a long-standing problem in the field of interfacial and membrane microrheology, but also provides a unique and highly desirable advantage for a variety of monolayer, thin-film, and membrane systems—SPIM is truly a noncontact measurement of the surface rheology. The bead is coupled to the monolayer purely hydrodynamically so that significant issues associated with the perturbation of the soft monolayer structure by the probe are entirely avoided. The SPIM method is ideal for studying intracellular microrheology since the probe particles are typically near the cell membrane or other internal fluid bilayers.

To make SPIM a quantitative measurement, one computes the response function of a submerged probe at a given depth below a viscoelastic monolayer. First, a response function is computed of a sphere of radius a submerged at a depth d below a free air/water interface. This result is compared to fluctuation data from that system (e.g., see FIG. 8, which provides a plot of the ratio of the imaginary part of the response function to the Stokes' value for the bulk response function for both a free air-water interface and a glass-water interface). The data agree with the essentially well-understood low Reynolds number problem, therefore validating the analysis of the experimental results. The effect of surface tension and bending elasticity of the interface also needed to be considered. These effects are not important for the clean air/water interface since the bending energy is negligible and the surface tension is sufficiently high so as to keep the surface essentially flat. But, these effects need to be considered in order to understand the role of induced undulations of the interface due to the motion of the probe in the plane parallel to the un-deformed interface for monolayers with smaller surface tensions and finite bending energies. Moreover, as already provided herein, this calculation is useful for biological applications where nearby membranes may be at low tension and have significant bending energies.

The response function of a bead submerged below a viscoelastic monolayer is also determined. The resulting response function, while complicated, has at least one simple limit; if the surface tension is large enough so as to approximate the membrane as flat, and for a sufficiently large monolayer (2d) viscoelastic shear modulus $\mu(\omega)$, the effect of that viscoelastic layer on the response function depends on a correction term of order $a/|l(\omega)|$, where $l(\omega)= \mu(\omega)/\omega\eta_{water}$ is the viscoelastic analog of the Saffman-Delbrück length and a is the radius of the probe particle. The data for three different monolayer systems (e.g., see FIG. 3), demonstrates that that the method of the disclosure is able to reproduce the previously measured viscosities for two very different types of monolayers: DPPC, which has an increase in viscosity with surface pressure, and eicosanol, which has a decrease in viscosity with surface pressure. Thus, a device comprising the microrheological methods of the disclosure has a dynamic range of at least 2.5 orders of magnitude. In another embodiment, the device comprising the microrheological methods of the disclosure has a dynamic range of at least 3, at least 3.5, at least 4, at least 4.5, at least 5, at least 5.5, at least 7.5, or at least 10 orders of magnitude. It should be understood that for the greater orders of magnitude for the dynamic range the device can also test more rigid monolayer systems, such as heneicosanoic acid, which may not be measurable at lower orders of magnitude for the dynamic range.

Figure 4:
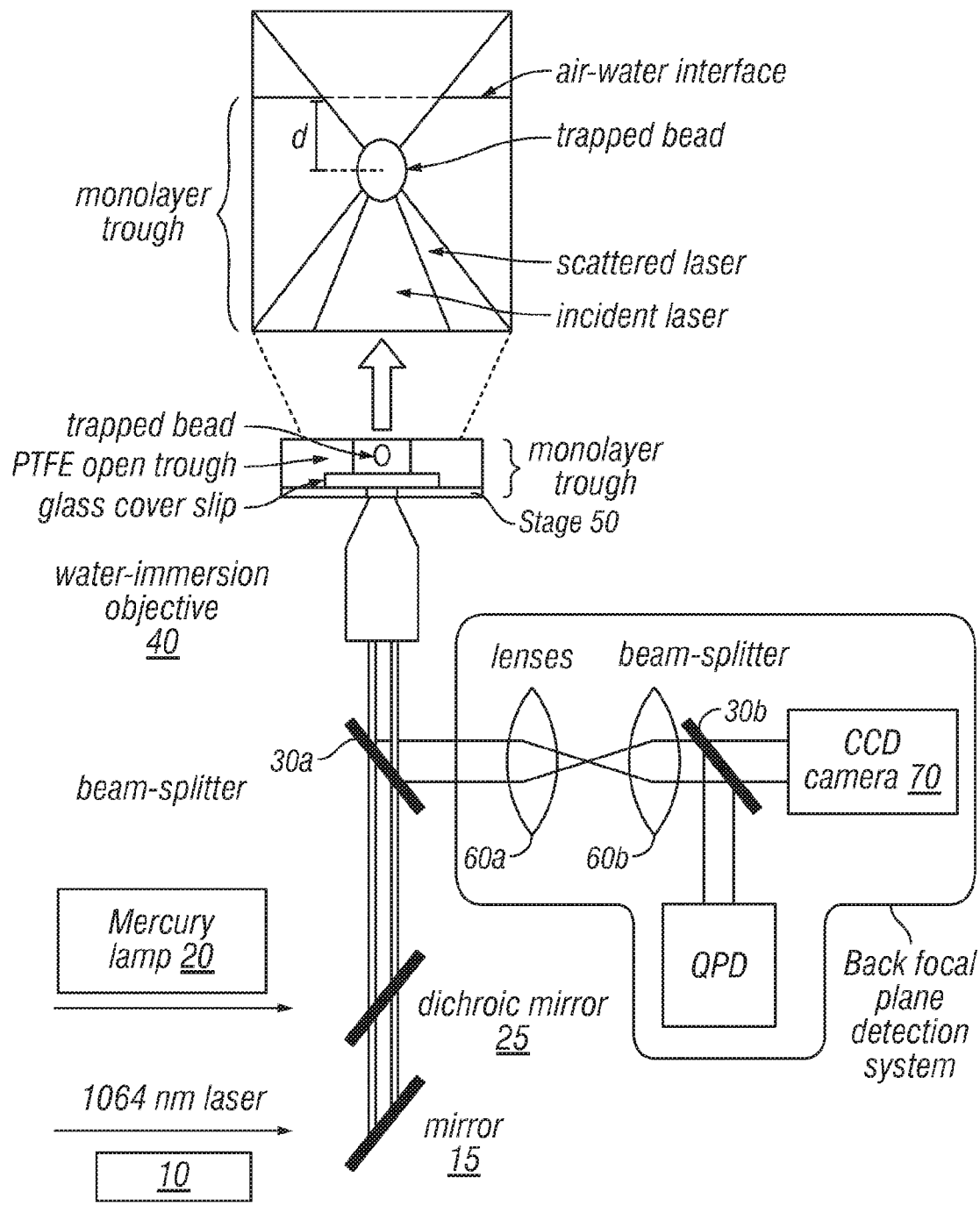
FIG. 4 provides a schematic of the position detection and imaging system. The inset shows a particle (with radius R) trapped a distance d below the air/water interface. This distance is measured from the center of the particle to the interface.

Experiments were performed using a customized Langmuir trough that has an integrated optical tweezer/quadrant-photodiode system, which is coupled to the monolayer from below through a water emersion objective. The objective is used to form the optical trap, and the reflected light is collected by the objective and focused on a quadrant-photodiode (QPD) for measurement of the positional fluctuations of a particle in the optical trap. Although the beads can be of different radii; typically, beads of radii 0.5 to 5 µm are used. The beads are trapped near the surface. The position of the bead relative to the surface can be stepped in small increments (e.g., 5 µm increments) using, for example, laser tweezers. FIG. 4 provides a schematic of a device comprising noncontact microrheological methods of the disclosure which can be used to measure positional fluctuations of a particle embedded in a monolayer.

As has already been provided herein, there are two sources of systematic error due to the use of reflected-light geometry. While the disclosure has already provided for measurements to correct for these errors, the disclosure further provides for a transmission based instrument that does not generate these errors. In a certain embodiment, for cellular systems the corresponding reduction in reflections can use the corrective measurements presented herein for correcting the two reflected-light geometry sources of systematic error.

The disclosure provides for a device comprising microrheological methods of the disclosure that can correlate bulk tissue mechanics with local micro-environment mechanics in engineered extra-cellular matrix (ECM) tissues, such as the mechanical properties of the endothelial glycocalyx and the fibrin microenvironment. In particular embodiment, a device comprising microrheological methods of the disclosure can generate shear gradients within naturally derived hydrogels. The shear gradients lead to stiffness gradients within naturally derived hydrogels, such as fibrin. The stiffening of the ECM near invading capillaries during capillary morphogenesis was measured with a device of the disclosure, demonstrating that covalent attachment of VEGF to an engineered scaffold extends the lifetime of VEGF signaling can me measured while preserving signaling potency.

Provided herein are microrheological methods, such as using passive (PMR) and active (AMR) modes of microrheology, which interrogate the local viscoelastic properties of 3D ECMs. In a certain embodiment, microrheological methods disclosed herein can correlate changes in cell phenotype with bulk material properties. In a further embodiment, microrheological methods disclosed herein can quantify the local mechanical microenvironment on a length scale relevant for cells and their adhesive complexes. In yet a further embodiment, microrheological methods disclosed herein can make measurements in 3-D culture systems. As is further provided in Examples herein, microrheological methods disclosed herein have utilized MR within transparent hydrogels such as collagen, fibrin, PEG-fibrinogen, and reconstituted basement membranes (rBM, Matrigel™).

The disclosure shows that the discrepancy between microscopic fluctuation data and those obtained from more traditional, active mechanical measurements, can be solved by correctly characterizing the response function, in particular correcting for the nature of the coupling between the probe particle and the monolayer. The disclosure further provides that accurately computing the response function involves addressing a number of physics issues that have been identified for particles embedded in interfaces, including the role of the subphase, the contact angle between the particle and the interface, and changes in the monolayer itself induced by the particles. Current methods minimize these effects, by using techniques for probes embedded in a monolayer involving active methods that focus on thin-disks. By contrast, the disclosure provides novel and non-obvious microrheological methods to accurately model particles embedded in surfaces using a non-contact approach to microrheology of interfaces, by observing the fluctuations of particle a few particle radii into the subphase and not in the monolayer itself. The disclosure also provides for a microrheological method which contemporaneously eliminates the issues associated with tracer-induced structural perturbations of the monolayer and avoids the complexities of the three-phase contact line by simplifying the nature of the coupling between the monolayer and the probe. A microrheological method disclosed herein, has introduced a new, and therefore novel, set of physics to solve these issues by sacrificing the coupling strength between the probe and monolayer.

The disclosure provides a non-contact microrheological method to determine membrane and interfacial microrheology, where the measurement of the fluctuations of submerged tracers as a function of their depth is used to infer the viscoelastic properties of the monolayer above them. The term "depth" as used herein refers to the absolute value of the distance from the center of the particle to the air/water interface.

The microrheological methods disclosed herein have significant advantages over current methods by eliminating issues associated with the direct interaction of the tracer and the fragile monolayer. The disclosure further provides microrheological methods which use a calculation of the submerged particle response function, which function relates the fluctuation data to the interfacial modulus. The non-contact microrheological methods of the disclosure provide in the Examples herein, the use of the method with three monolayers: dipalmitoylphophatidylcholine (DPPC), arachidic acid (AA), and eicosanol. The results therefrom were consistent with previous macroscopic measurements. Moreover, the methods disclosed herein can be tuned so that the measurements can be used to obtain even lower surface moduli.

The disclosure further describes significant and quantitatively differences between the fluctuation measurements beneath a free surface that does not support shear stresses (free air/water interface) and an infinitely rigid (water/glass interface) one. As all rheologically interesting monolayers fall between these two extremes, measurements from the microrheological methods presented herein, set the range of all possible surface rheology outcomes using submerged particle microrheology. By using these extreme cases, the microrheological methods presented herein experimentally verify the theoretical analysis of the response functions that account for submerged particle explorations of monolayers and membranes.

In a particular embodiment, the disclosure provides a microrheological method comprising the step of measuring the fluctuation of a particle by using a weak laser trap in combination with a back focal plane displacement detection scheme, such that the particle is held at a fixed depth below the interface and its small (e.g., few nanometer scale) fluctuations in a plane parallel to the surface is measured. In a further embodiment, a microrheological method disclosed herein further comprises the step of extracting from the fluctuation measurements the in-plane response function of the tracers. The disclosure further provides a microrheological method disclosed herein, where any back scattering artifacts generated from the position of the tracer particle being determined by back scattered light from the tracer and the nearby interface, can be minimized or accounted.

In a particular embodiment, the disclosure provides a microrheological method that can account for the optical complexities of working with a laser trap near the interface in order to recover the Stokes result at depth, wherein the method observes the expected changes in the tracer's mobility that is consistent with hydrodynamic calculations. Accordingly, the disclosure provides a microrheological method that provides a response function that can be used to account for the role of surface tension and particle size for a variety of applications, including in the technical fields of materials science, engineering, geophysics, physiology, human biology, food science, and pharmaceuticals. Additionally, microrheological methods of the disclosure have sufficient sensitivity to make reproducible rheological measurements of complex viscoelastic monolayers in spite of the weakened hydrodynamic coupling between the tracer and that monolayer can so as to measure the dependence of the tracer particle's mobility as a function of depth.

The effect of a nearby rigid wall on the drag coefficient of a particle presents a problem in low Reynolds number hydrodynamics, and is of particular interest to microfluidics. Typically, it has been presumed that the presence of a wall reduces the mobility of the particles near to it. The disclosure presents Examples that rebut this presumption by presenting that a free surface enhances the mobility of the particles near to it. The key distinction is that previous investigators have considered the effect of rigid walls under stick boundary conditions—the fluid velocity is required to vanish at the surface of the wall. The disclosure, by contrast, provides one or more Examples herein with (1) a zero shear stress boundary condition, and (2) a condition that the normal stress is consistent with the effects of surface tension on the fluid vapor interface. Because the distinction between the effect of a rigid wall and a zero shear stress wall is so dramatic, there is a significant range available to observe the effects of complex surface rheology as a function of frequency.

The disclosure provide a device for SPIM implementation. The device comprises an automated microscopy system comprising an automated stage, at least one water immersion objective, an illumination light source (e.g., a lamp), a laser, at least one mirror, various lenses and a camera (e.g., a CCD array or CCD camera). Features of the device include a laser trap system for particle manipulation and a quadrant photo-diode system for detection of particle motions. For example, turning to FIG. 4, a schematic of a device of the disclosure is depicted. In the Figure a laser 10, a light source/lamp 20, a first mirror 15, a second mirror 25, a beam splitter 30a and 30b, an objective lens 40 a stage (comprising s sample, e.g., a cover slip) 50, a plurality of lens (60a and 60b) and a camera 70 (e.g., a CCD camera) are depicted.

Furthermore, the system can comprise a computer that control the stage, laser, lamp output, objective and CCD camera. In addition, the computer can comprise computer implemented instructions for controlling the stage, laser, lamp output, objective and CCD camera. The image data obtained from the CCD camera can be relayed digitally to the computer for processing using the methods described herein.

A number of modifications to the basic instrument can be made to achieve certain embodiments. For example, modifications can be made to obtain a transmission mode, an active manipulation of probe particles, and a scanning mode. Individually, these modifications involve established technologies currently utilized in the laboratory.

In the Examples presented herein, the depth dependent changes in the imaginary response function, and thus, the mobility, of a submerged particle was calculated. By comparing the experimental data with the theoretical prediction for the free interface of water, the increase in the imaginary response near the surface is in good agreement with the experimental data (e.g., see FIG. 7). This increase is due to the fact that the motion near the free surface leads to less viscous dissipation. The agreement confirms the correct identification of the role of particle size and surface tension. The calculation presented herein, establishes that particle size is a higher order effect, allowing the use of relative large 5 µm particles, and that surface tension introduces a reactive part of the response function near the free surface since the elastic deformation of the interface does recoverable work. It could be expected, however, that the effect of surface tension is vanishing small for high surface energy interfaces because the large surface tension forces the surface to remain nearly flat. The relevant measure of effect of surface tension, T, on the response function of a tracer of radius a is controlled by the capillary number $Ca=\eta a(2\Pi f)/T$. For the air/water interface at the frequencies of experimental interest, $Ca \ll 1$ so the interface remains at and surface tension should produce no measurable change in the response function. Indeed, no observation of a surface tension effect was found in the Examples presented herein.

In order to understand the physics and confirm the hydrodynamic calculations, two divergent limitations were tested: a perfectly rigid surface and a free and deformable surface. The Examples provide herein provide a proof of principle in that one can extract the complex frequency dependent rheology of a viscoelastic interface, such as a Langmuir monolayer, from observing the in-plane fluctuations of tracers submerged a short distance below it. The out-of-plane fluctuations provided an excellent measure of the bending mechanics of the interface as well. The non-contact microrheological method disclosed herein provides great utility to those in the art, since the presence of the submerged probe particle should in no way perturb the monolayer, thus eliminating the need for more difficult two-particle microrheology. Moreover, the (purely hydrodynamic) methods disclosed herein by coupling of the probe to the monolayer eliminates the need to understand the complex physics of the three-phase contact line in order to interpret the fluctuation data rheologically. Using the other methods known in the art, the interaction of the probe and monolayer domains may govern the measured rheological response, rather than the rheology of the monolayer, e.g., depending on the measurement technique, shear thickening or shear thinning may be observed in the same system. In addition, it appears that for the case of highly elastic monolayers, probe particles are typically expelled from the monolayer presumably due to the elastic stress they produce at the interface. This effect likely accounts for the large and consistent discrepancies between fluctuation-based and active mechanical measurements of such monolayer systems.

The following examples are intended to illustrate but not limit the disclosure. While they are typical of those that might be used, other procedures known to those skilled in the art may alternatively be used.

EXAMPLES

Materials

Apparatus: The device to test the microrheological methods of the disclosure involves two main systems: the optical components that generate the trap and measure the particle fluctuations and a small cell for holding the fluid samples. With both of these elements, an existing Langmuir monolayer trough coupled with a 100× water immersion objective (NA 1.0, Olympus America Inc.) from below the trough was utilized. The optical trap uses a Nd:YVO4 laser (Spectra Physics BL-106C, 1064 nm). The laser light passes through an optical system consisting of a beam expander, steering lenses and mirrors, leading to the water immersion objective, which focuses the beam to form an optical trap. The trough is attached to a vertical translation stage so that the fixed objective can trap particles at various distances below the surface. Trapped particles scatter laser light back through the objective, onto both a quadrant photodiode (New Focus 2903) and an intensified CCD camera. The quadrant photodiode (QPD) allows high frequency (66 kHz) 2-dimensional position measurements to be recorded via a data acquisition board and custom Labview software. A schematic of the apparatus is provided in FIG. 4.

Measurement of Monolayer Viscosity Using Non-Contact Microrheology.

The velocity response function was calculated for a spherical particle of radius a in a fluid with viscosity q submerged at depth d beneath a monolayer (e.g., see FIG. 1). The particle oscillates at frequency $\omega$. Given the relevant capillary number for monolayer systems of interest ($Ca=\eta V_0/\tau \sim 10^{-6}$), the vertical deflection of the interface was neglected as these corrections are generally small. At the relevant frequencies (<100 kHz) fluid inertia may be neglected and the Stokes equation was used for the fluid velocity field v:

$$\nabla p - \eta \nabla^2 v = f \quad (2)$$

$$\nabla \cdot v = 0 \quad (3)$$

where p is the hydrostatic pressure that enforces the fluid incompressibility and $f=Fe^{i\omega t}\delta(z+d)\delta(x\perp)$ is the applied oscillatory point force representing the probe, with $x\perp=(x,y)$ the lateral position vector. To study the fluctuations of the tracer in the plane parallel to the monolayer $F\|\hat{x}$ was used. A more general solution for a complex force distribution can be found by superposition. A coordinate system was chosen such that the fluid was of infinite lateral extent, and infinite depth in the −z direction, bounded by the monolayer interface at z=0.

The fluid velocity vanishes far from the point of force application, and, in the absence of height undulations, the fluid velocity $v_z$ was perpendicular to the surface vanish at the interface. There, a no-slip condition was imposed relating the displacement field of the viscoelastic monolayer u to the fluid velocity v; since the work was primarily in the frequency domain this implied that $v_\alpha|_{z=0}=-i\omega u_\alpha$, where Greek indices run over the coordinates x and y only. Stress balance in the interfacial monolayer required:

$$\mu \partial^2 u_\alpha + (\mu+\lambda)\partial_\alpha \partial_\beta u_\beta + \frac{1}{2}\eta(\partial_\alpha v_z + \partial_z v_\alpha)|_{z=0} = 0 \quad (4)$$

where the Lame constants $\lambda,\mu$ must be interpreted as complex, frequency-dependent quantities. The two first terms correspond to the stresses induced by strain (and strain rate) in monolayer which must balance the hydrodynamic stresses from the subphase in the third term. The limit $\lambda \to \infty$ corresponds to an incompressible monolayer.

Eqs. (2), (3), and (4) were solved subject to the noslip boundary condition in order to determine the velocity amplitude of the tracer sphere V in response to the applied force. To do so, the solution was divided into two parts. The first part $v^{(1)}$ satisfies the force balance in the bulk, but perfect slip at the surface. This velocity field did not satisfy the matching condition, and thus induced unbalanced stresses on the surface. To correct this, a second solution $v^{(2)}$ was added, which is the fluid velocity field induced by the negative of these stresses and satisfying the homogeneous equations, Eqs. (2) and (3) with f=0. By superposition, the sum of these two velocity fields is the physical solution, which satisfies all the necessary stress balance conditions in the subphase and in the interface. Associated with each bulk velocity field $v^{(1,2)}$ there was an in-plane membrane displacement $u^{(1,2)}$ determined by the no-slip matching condition, and from which the interfacial displacement field can be computed.

$v^{(1)}$ was chosen to be the solution given by a single point force in the bulk and the associated "image" force reflected about the z=0 plane. The resultant velocity field was written using the Green's function of a point force in an infinite fluid and gives the hydrodynamic response of the subphase to the applied point force assuming that the interface at z=0 can exert no shear stresses.

That perfect slip solution was $$v_j^{(1)} = \frac{F_x}{\eta k^2}(\delta_{xj} - \hat{k}_z\hat{k}_j)\cos(k_z d) \quad (5)$$

$$u_\beta^{(1)} = \frac{F_x}{2\eta\omega i}e^{-k_\perp d}\left(\frac{-2\delta_{x\beta}}{k_\perp} + \frac{k_x k_\beta}{k_\perp^3}(1+k_\perp d)\right) \quad (6)$$

in the Fourier domain, where k and $k_\perp$ are three and the two dimensional (in the plane of the interface) wavevectors respectively. By symmetry, the velocity field $v^{(1)}$ vanishes at the surface (z=0), so that the associated normal displacement was zero, $u^{(1)}=0$. Projecting the in-plane components of the interfacial velocity into longitudinal and transverse channels, $u_\beta = u_\beta^{(L)} + u_\beta^{(T)}$, was found $$u_\beta^{(L1)} = L_{\beta\alpha}u_\alpha^{(1)} = -\frac{F_\alpha}{2\eta\omega i}e^{-k_\perp d}\left(\frac{k_\alpha k_\beta}{k_\perp^3}(1-k_\perp d)\right) \quad (7)$$

$$u_\beta^{(T1)} = T_{\beta\alpha}u_\alpha^{(1)} = -\frac{F_\alpha}{\eta\omega i}e^{-k_\perp d}\left(\frac{\delta_{\alpha\beta}}{k_\perp} - \frac{k_\alpha k_\beta}{k_\perp^3}\right) \quad (8)$$

using the two-dimensional longitudinal and transverse projection operators $L_{\alpha\beta}=k_\alpha k_\beta/k_\perp^2$ and $T_{\alpha\beta}=\delta_{\alpha\beta}-L_{\alpha\beta}$. Using Eq. (4) and noting that the fluid stresses on the interface due to $v^{(1)}$ vanish by construction, it was found that the $v^{(1)}$ solution generates unbalanced interfacial stresses $$S_\alpha^{(L)} = -k_\perp^2(2\mu+\lambda)u_\alpha^{(L1)} \quad (9)$$

$$S_\alpha^{(T)} = -k_\perp^2 \mu u_\alpha^{T1} \quad (10)$$

Since the membrane must be stress-free, counter stresses were applied to the interface to cancel these unbalanced stresses due to the $v^{(1)}$ solution. Those counterstresses generated the fluid velocity correction in the subphase due to the surface rheology of the interface—specifically how it differs from that of a perfect slip interface assumed in the calculation of $v^{(1)}$. It was then straightforward to calculate the real-space subphase fluid velocity induced by longitudinal and transverse modes of the membrane using the appropriate Green's functions derived as:

$$v_\alpha^{(L2)} = i\omega \int S_\alpha^{(L)} \frac{(1+k_\perp z)e^{ik_\perp \cdot x_\perp + k_\perp z}d^2 k_\perp}{(2\mu+\lambda)k_\perp^2 - 2i\omega\eta k_\perp (2\pi)^2} \quad (11)$$

$$v_\alpha^{(T2)} = i\omega \int S_\alpha^{(T)} \frac{e^{ik_\perp \cdot x_\perp + k_\perp z}d^2 k_\perp}{\mu k_\perp^2 - i\omega\eta k_\perp} \frac{d^2 k_\perp}{(2\pi)^2}. \quad (12)$$

Performing the remaining integrals, the velocity field correction $v^{(2)}$ was determined at the position of the tracer and Faxén's law was used to find its contribution to the velocity of that particle. Adding the two contributions, the result was written using the susceptibility matrix $x_{ij}$ relating position $U_i$ of the tracer to the applied force $F_j$ $$U_i = V_i/(-i\omega) = x_{ij}F_j \quad (13).$$

Taking the limiting case of an incompressible monolayer, the main theoretical result was found. The in-plane part of the response function was given by $$\frac{X_{xx}}{X^\infty} = 1 - \frac{9}{16d} + \frac{1}{16d^3} - \frac{3}{2l}\left[Ei\left(\frac{-2\bar{d}}{\bar{l}}\right) - i\pi\right]e^{\left(\frac{2d}{l}\right)} \quad (14)$$

With $Ei(x)=\int_{-\infty}^x (e^t/t)dt$ being the exponential integral function. $X^\infty=i/6\pi a\eta\omega$ was defined to be the usual Stokes susceptibility valid for the spherical tracer only when infinitely deep below the interface, and $l=\mu/(-i\eta\omega)$ to be the Saffman-Delbrück (SD) length. For a purely viscous monolayer, this length was simply the ratio of viscosities between the bulk and membrane, but generally it is more complex for viscoelastic monolayers. Its modulus sets the length scale over which in-plane monolayer momentum is transferred to the fluid subphase; it thus serves as a cut-off for the logarithmic divergence that appears in two-dimensional over-damped hydrodynamics. Using the particle's radius to non-dimensionalize lengths, was defined as $\bar{d}=d/a$ and $\bar{l}=l/a$.

For tracers at depths much greater than the SD length d/|l|>>1, the response function is dominated by dissipation in the subphase. In this limit, the response function separates into two terms:

$$X_{zz} \approx X^{Glass}(\bar{d}) + \frac{3}{d}X^{Mem}\left(\frac{3l}{4d}\right).$$

The first contribution was equal to the response function of the particle below a rigid wall with no slip boundary conditions (e.g., a glass cover slip)

$$X^{Glass}(\bar{d})/X^0 = 1 - \frac{9}{16d} + \frac{1}{16d^3} + O\left(\frac{1}{d}\right)^4.$$

The second contribution was the susceptibility of the particle embedded directly in the (incompressible) interface:

$$X^{Mem}(\bar{l})/X^{Stokes} = \frac{3}{2}\frac{1}{\bar{l}}\log\left(1 + \frac{2\bar{l}}{3}\right),$$

but with an effective SD length: $l \rightarrow l/d$.

The regime dominated by surface rheology $d/l<<1$ was more germane to the study. In this limit it was found that Eq. (14) simplifies to $$\frac{X_{xx}}{X^0} \approx 1 - \frac{9}{16d} + \frac{1}{16d^3} - \frac{3}{2\bar{l}}\left[\gamma - i\pi + \log\frac{2d}{\bar{l}}\right] \quad (15)$$

where $\gamma$ is the Euler-Mascheroni constant.

At large distances from the interface $\bar{d} \geq 10$, the susceptibility approaches that given by the simple Stokes drag on a sphere independent of the value of the SD length. Such distant tracers were useless rheological probes. The key microrheological measurement involved studying how this susceptibility varied as the tracer's depth was decreased. For l<1 the particle response increased as the distance decreased, while for large SD lengths (l>1) the susceptibility decreased (e.g., see FIG. 2A,C). The inverse of the nondimensionalized SD length had a qualitative analogy to an effective Knudsen number, or partial slip length, although quantitatively the limit of perfect slip was never achieved in this result due to the assumption of surface incompressibility.

The phase of the complex SD length was determined by whether interfacial stresses were dissipative or reactive. The plot of the response function for the two extreme cases of a purely elastic monolayer where l was imaginary, and the purely viscous one where l was real in presented in FIG. 2. As can be seen in FIG. 2A,C the imaginary part of the susceptibility does not vary much between the two extreme cases and is mainly dependent on the magnitude of the SD length.

The real part, on the other hand, acquired a finite value when the surface was elastic but vanished for purely viscous surface. Although it has been assumed up to this point that the capillary number as Ca<<1, it was straightforward to calculate the leading order effects of lowering the surface tension. These surface height undulations resulting from finite Ca have a subdominant effect on the tracer response for in-plane motion, but in the case where determining vertical fluctuations was necessary they played an important role.

To demonstrate the utility of submerged particle microrheology the fluctuation spectrum of tracers was observed at various depths below three different surfactant monolayers: dipalmitoylphosphatidylcholine (DPPC), arachidic acid (AA), and eicosanol. These systems were selected since they have been well studied macroscopically, and all three show large changes in surface viscosity with area pressure. DPPC has a low pressure/low viscosity phase and Eiconsanol has low pressure/high viscosity phase. AA is sufficiently viscoelastic to mimic a rigid boundary.

In short, the tracer was trapped at a given depth below the surface using laser tweezers, and the light scattered off the particle with a quadrant photodiode was analyzed to measure its thermally driven position fluctuations. By observing the change in the 5 μm radius tracer's fluctuations (in the plane parallel to the interface) as a function of depth below the surface in a frequency band of 100 Hz around f=ω/2π~$10^3$ Hz and using the fluctuation-dissipation theorem, the imaginary part of the tracer's response function was measured. The response function was measured at depths of d~1-100; data taken at depths d>25 were great enough to yield the Stokes result; these were used to normalize the response function at shallower depths. The imaginary part of the response function as a function of depth is then fit using Eq. 14 using |l| as the only adjustable parameter. All three monolayers were assumed to be purely viscous, which makes l a real number.

Figure 3A:
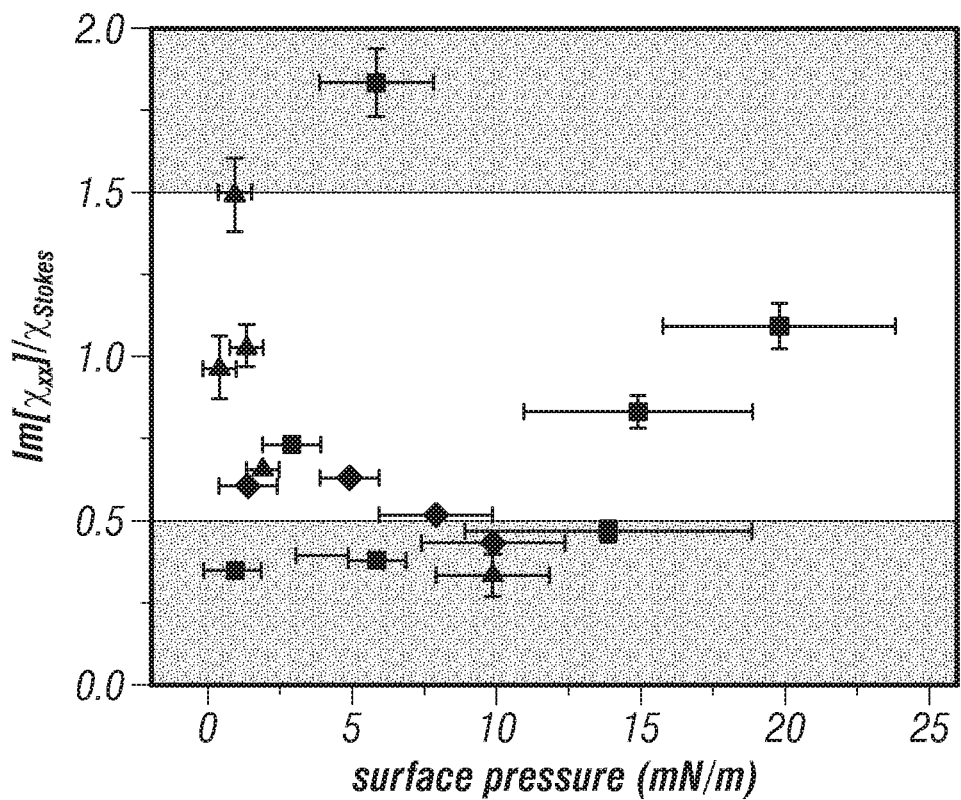
FIG. 3A-B presents experimental results for tracer susceptibility near monolayers and their conversion to membrance viscosity for DPPC (black triangles), AA (red circles), and eicosanol (blue squares). (A) The normalized susceptibility at d~2 from the interface. (B) The susceptibilities are converted to viscosities by the results shown in FIG. 2. The yellow areas represent regions that are excluded by theory—see text. The values of and observed variations in the surface viscosity are consistent with macroscopic measurements.
Figure 3B:
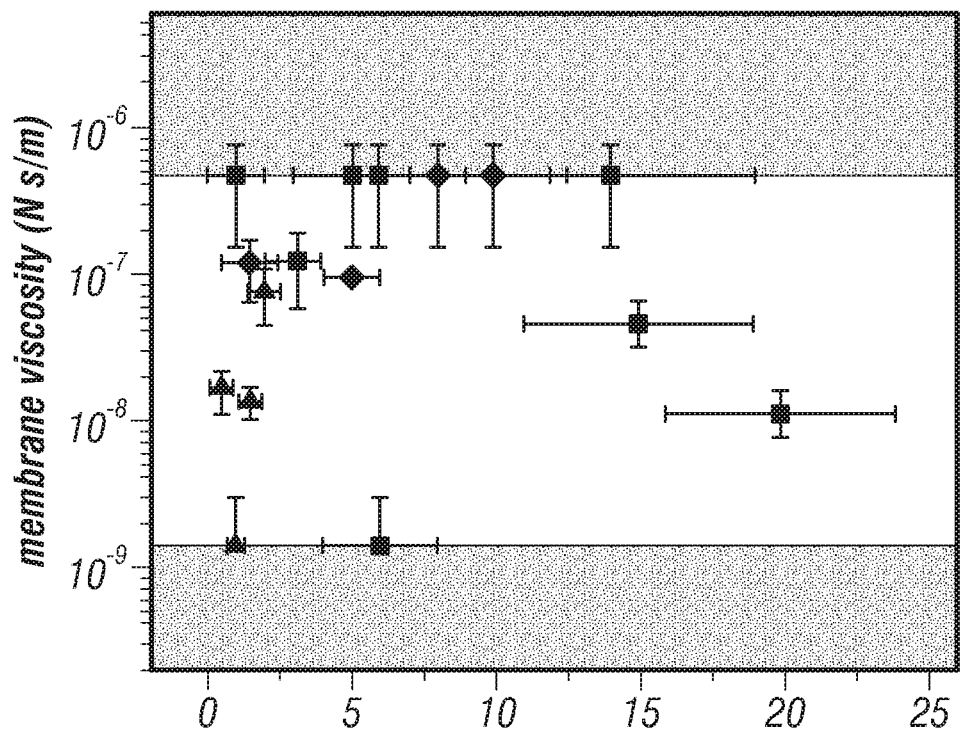

In FIG. 3, the results of these measurements for the imaginary part of the tracer response function normalized by the Stokes result for tracers submerged below DPPC (black triangles), AA (red circles), and eicosanol (blue squares) monolayers as a function of surface pressure. In FIG. 3B these data were converted into the inferred surface viscosities. The findings were consistent with the previously measured trends with surface pressure and were of the correct order of magnitude for all three systems, demonstrating that there was no "missing modulus" in the microrheological measurements. The lower values of surface viscosity observed were below those which can be measured macroscopically. The yellow areas presented in FIG. 3 represent regions that were excluded by the theoretical predictions that correspond to the frequency range, assumption of incompressibility, depths that were accessible, and the radius of the tracer. The frequency band and tracer size control the range of accessible viscosities, while depth specificity directly affects the resolution of the measurement; these parameters can all be modulated experimentally, thus giving access to different ranges of viscosities.

Non-contact particle microrheology exploits a purely hydrodynamic coupling between the tracer and the monolayer. At the expense of this weaker coupling, one avoids issues associated with understanding the complex interaction of the probe and the monolayer. As presented herein, this weaker coupling is sufficient to obtain rheological data in this purely non-contact mode and to measure the viscosity of very low surface viscosity systems.

Systems with complex viscoelastic responses and exploration using the submerged tracer in a lateral scanning mode to detect spatial variations in surface rheology in inhomogeneous monolayers and membranes are also encompassed by the methods presented herein. The results also demonstrate that intracellular microrheological data taken near viscous cell membranes have to be corrected for this proximity effect.

Probing Interfacial Dynamics and Mechanics Using Submerged Particle Microrheology.

As originally designed, the objective extends through a well in the bottom of the Langmuir trough. The optical trap would be focused near the air/water interface and used to trap particles in or near a Langmuir monolayer. However, for the experiments reported here, two smaller sample cells were used to eliminate flows in the subphase and allow for ease of switching between free and rigid boundary conditions for the interface. The Langmuir trough was used as a sample stage to support the cells, and allowed for immersion of the objective in water so that it functioned properly. For experiments with a free boundary, the cell consists of a thin block of polytetrauoroethylene (PTFE) with a circular hole, 19 mm in diameter. A glass cover slip is attached to the bottom of the Teflon chamber with double sided tape to form an open, thin cylindrical cell about 2 mm in depth. The solution fills this volume to a height of approximately 1 mm, which is shallow enough to allow the objective access to the air/water interface. A cover was used to reduce air currents across the interface.

For studies of a rigid interface, the fluctuations of trapped particles in a ~50 μL were measured in a chamber made from two layered strips of double sided tape sandwiched between a glass slide and a glass coverslip. The chamber was approximately 190 μm thick and was filled with the same diluted particle solution as was used in the air/water interface experiments. The chamber was rested on the Langmuir trough, just like the air/water interface cell, with the coverslip side of the chamber facing downward toward the objective. The trapped particle's depth was defined as the distance below the glass slide, which was the glass/water interface furthest from the objective. A similar chamber was used to obtain the data shown in FIG. 10, but with polycarbonate in place of a glass slide.

Figure 5:
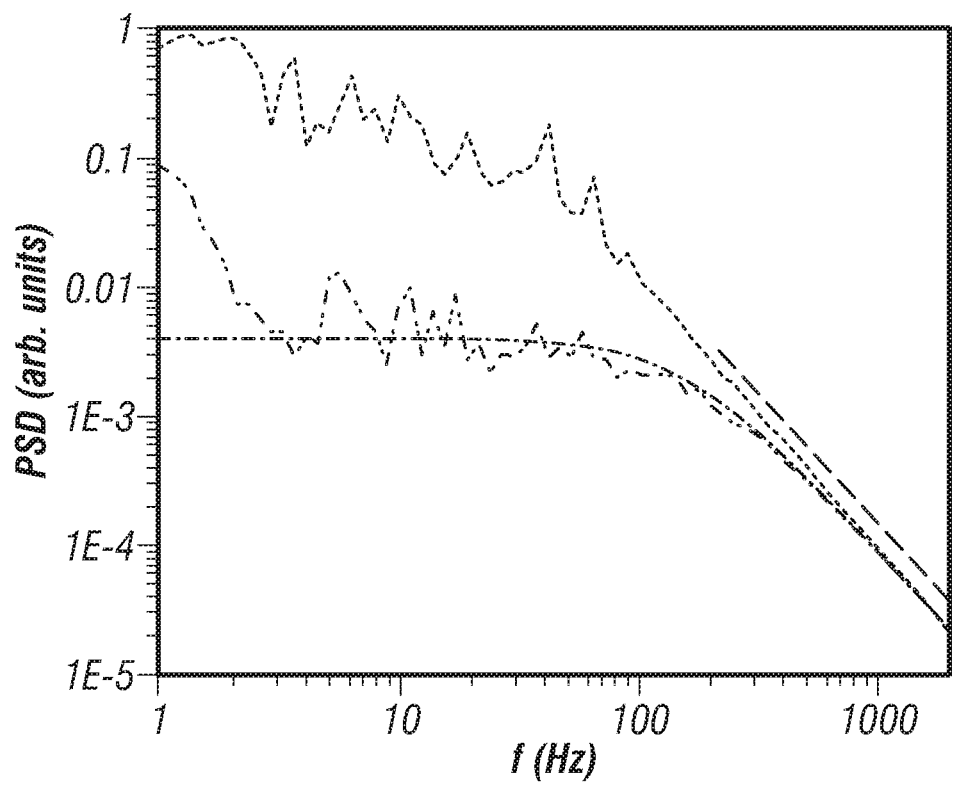
FIG. 5 presents a plot of the power spectral densities (PSDs) of 0.5 μm (green) and 5 μm (orange) radius particles. A Lorentzian fit to the spectrum of the red for the 0.5 μm radius particle—see Eq. 1—is shown in red. This fit shows that the data are consistent with a simple model of overdamped motion in a linearly elastic trap. On the other hand, the PSD of the 5 μm radius particle poorly fits a Lorentzian. The larger particle requires higher laser power (100 mW instead of 20 mW) for trapping and this introduces more low frequency noise. In addition, the high-frequency Brownian motion of larger particles is of a smaller amplitude than for the smaller ones and consequently harder to detect. For this reason, the observed PSD (above) for that particle beyond 2000 Hz decays more sharply than the expected 1=f2 (dashed line).
Figure 9:
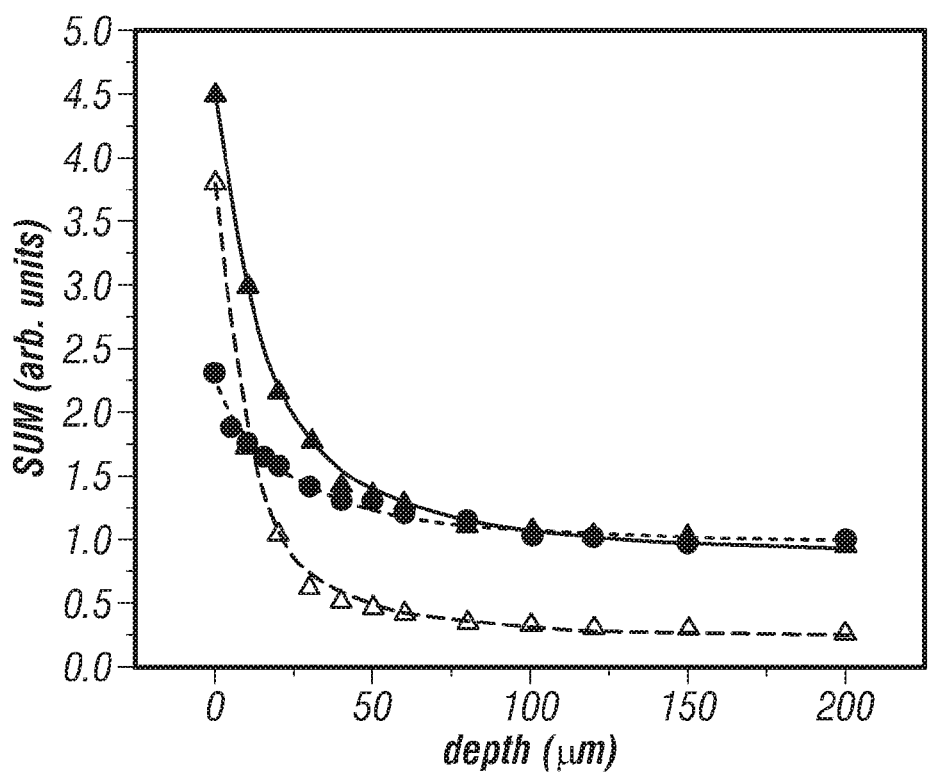
FIG. 9 presents a plot of the SUM signal, a measure of the total intensity on the quadrant photodiode (QPD), is plotted as a function of depth. The following are represented on the plot: a trapped 0.5 μm radius particle (solid black triangles), a trapped 5 μm radius particle (solid blue circles), and the result without a particle (open black triangles). In the data with a particle trapped, a single particle is trapped throughout the measurement. The red lines are fits to the data of the form $$\frac{A}{(d/B+1)^2} + C.$$
Figure 10:
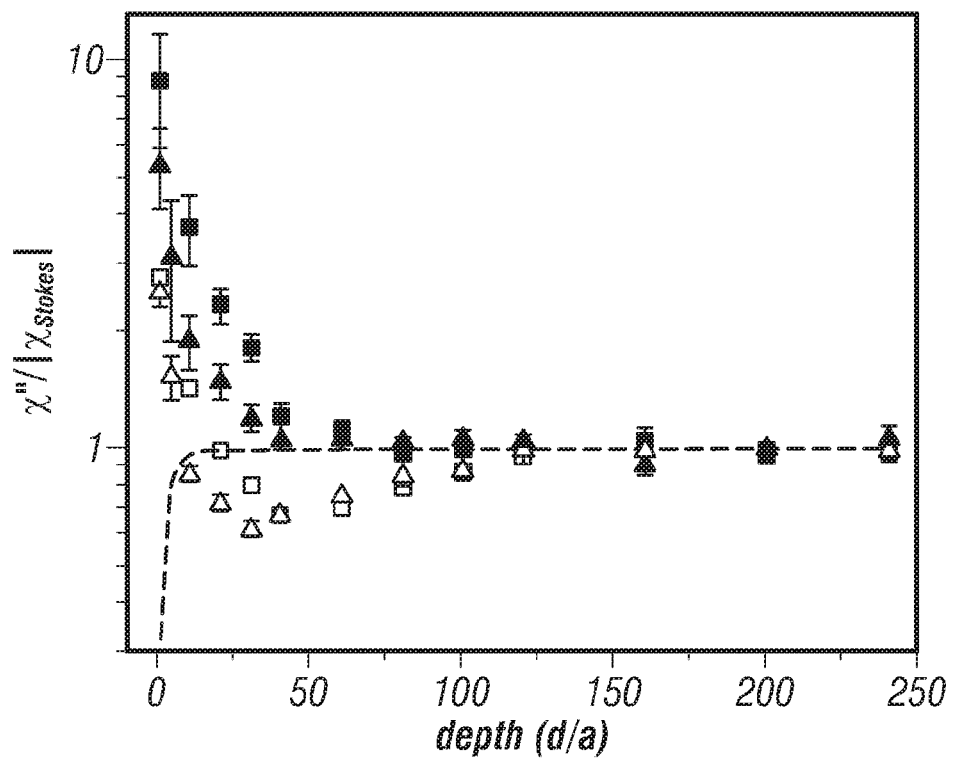
FIG. 10 presents a plot of the imaginary response function of 0.5 μm radius particles naïvely near a wall with stick boundary conditions calculated with normalization by the bulk SUM signal (solid symbols) and with normalization by the SUM signal at each individual particle depth (open symbols). To better understand the role of surface reflections, data from particles near walls made of two optically different materials: polycarbonate (η~1.592) and sodalime glass (η~1.520), represented by green and blue symbols respectively are presented. The red line is the expected result due to Faxèn's theory. Using the bulk SUM signal for normalization, the unphysical minimum near d~30a disappears. Despite this correction, the reflected light has an additional impact due to particle lensing that systematically increases the fluctuations near the surface. Since the index of refraction of polycarbonate differs from water more than does glass, the former materials generates more intense reflections, causing a larger variation in the position signal and resulting in a larger apparent mobility. The particle lensing effect is remedied by using sufficiently large tracer particles.

The cells were cleaned with water and ethanol prior to each experiment. For the open cell, before a sample was deposited, the cell was again filled with water, then aspirated to remove dust and other particles that may have entered the cell while waiting for the ethanol to completely evaporate. Carboxylate modified, red fluorescent particles (Invitrogen) were diluted in ultrapure water by a factor of $10^4$. This solution (0.3 mL) was placed in the circular cell. Two sizes of particles were trapped (0.5 and 5 μm radii as specified by the manufacturer), but the results from 0.5 μm particles were only used to highlight experimental difficulties with small particles and were not used in the final results. FIGS. 5, 9 and 10 contain results from these smaller particles. A mercury lamp excited the fluorescent tags on the particles, allowing them to be imaged by the CCD camera after passing through appropriate filters. With the particles in view, the trapping laser was turned on and a single particle was trapped. Prior to measuring the particle fluctuations with the QPD, a mirror was used to center the scattered light from the particle on the QPD's chip while the particle is 200 µm beneath the air/water interface.

A particle's position relative to the focus can be determined by comparing the images of trapped particles. For example, if a 0.5 µm particle is below the focus, the center of the particle appears dark; if above, it appears light. When a particle is trapped, it is located very close to the focus, has clear boundaries and no visible interference fringes. These phenomena can be used to find the surface in the following way. When a particle is trapped beneath the surface, a translation stage is used to lower the cell around the fixed objective lens, moving the optical trap carrying the particle closer to the water's surface. Video of the particle shows that it maintains its position relative to the focus throughout the vertical translation until the particle is pushed below the focus by the interface. At this point the particle appears with a black center and surrounded by interference fringes. The location of the surface can be confirmed by finding where the total intensity of scattered laser light is at a maximum. Once the location of the interface is determined, the objective is translated downward with an uncertainty in depth of approximately 5 µm in the air/water interface experiments. Between each fluctuation measurement at the air/water interface, the surface position is reacquired because of evaporation. The rate of evaporation was found to be on the order of 0.4 µm/minute, which would produce a significant error over the series of depth measurements if the surface were not reacquired.

Using the method discussed herein and in Walder et al. (*Review of Scientific Instruments* 2008, 79:063905+), a tracer position data was obtained at a rate of 66 kHz. Data for the lateral (e.g., in the plane whose perpendicular is the optical axis) displacements of the tracer particle form a time series $X_t$ of two dimensional vectors. The fast Fourier transform was calculated to obtain the power spectrum of these position fluctuations $<|x_f|^2>$ wherein f is the frequency variable conjugate to time t. Discounting the role of reactive stresses associated with surface deformation, the power spectrum takes the form $$\langle |x_f|^2 \rangle = \frac{D}{2\pi^2(f_c^2 + f^2)} \tag{16}$$

where $f_c$ is the corner frequency, which arises from the stiffness of the optical trap (e.g., see FIG. 5). All of the reported results were derived from measured time series with a length of 2 sec. The spectra of the fluctuations were blocked and averaged across many of such time series. The fluctuation data of 5.0 µm particles submerged below the air/water interface represent ~40 time series measurements. For the case of 0.5 µm particles at the glass and polycarbonate interfaces 10 and 5 time series were averaged respectively. Low frequency data showing drift were omitted from further analysis. We show power spectral densities ("PSDs") over a frequency range of 1 Hz to 2000 Hz. The lower limit was set by fluctuations in laser power on longer times scales while the upper limit was set by the ability to resolve small amplitude Brownian fluctuations of the relatively large sphere.

From the power spectrum we can directly compute the imaginary part of the response function. This response function describes the linear relationship between the position of the tracer and the force applied to it $$x_f = x(f)F_f \tag{17}$$

in a frequency-resolved (e.g., f-dependent) manner. It is generally applicable to viscoelastic systems. Writing this complex function in its real and imaginary parts was defined as $$x(f) = x'(f) + ix''(f). \tag{18}$$

The fluctuation-dissipation theorem immediately related the imaginary part of the response function to the PSD of the fluctuations via $$x''(f) = \frac{\pi f \langle |x_f|^2 \rangle}{k_B T} \tag{19}$$

The more common hydrodynamic quantity was the mobility of the particle, describing the linear relationship between the particle's velocity and the force applied to it. Of course, this quantity and the position response function defined above were directly proportional in the frequency domain. The advantage of discussing $\chi$, was that it related thermodynamically conjugate variables and thus entered the expression Eq. (19). Framing the results in this form also allowed a more direct connection to other microrheological analyses. A more complete discussion of the response function for the experimental system of the disclosure can be found in Shlomovitz et al. (*Physics of Fluids*, 2012), which teachings are incorporated herein.

The real part of the response function can then be found from a Kramers-Kronig integral. In practice, it was necessary to logarithmically block and bin the experimentally obtained PSD for smoothing purposes and the remaining integrals were performed using a discrete sine and cosine transform.

While it is true that the surface tension of the air/water interface introduced a reactive part to the particle's response function due to the elastic stresses associated with normal displacements of that interface, the calculations suggest that these effects are vanishingly small for high surface tension interfaces such as that of air and water. The experiments provided herein confirm that, within uncertainty, the real part of the response function is zero. Thus, in the two cases of current experimental interest (the air/water and water/glass interfaces), the particle's response function can be considered to be the combination of a purely dissipative and depth-dependent part due to the hydrodynamics and a simple elastic part due to the laser trap.

Hereafter the results are discussed in terms of the imaginary part of the response function defined in Eqs. (17) and (18). It is convenient when discussing these results to nondimensionalize them by the result expected for a spherical particle of radius a in bulk water of viscosity η:

$$X_{stokes} = \frac{i}{6\pi\eta a(2\pi f)} \tag{20}$$

For all experiments disclosed here, it can be expected that the imaginary part of the response function nondimensionalized in this way would approach unity as the depth of the particle increases.

To connect the QPD signals and the particle fluctuations, there were two main corrections due to two related optical effects: (1) changes in the background intensity of reflected light as the depth is changed, and (2) particle lensing effects acting on that reflected light. These corrections are discussed further herein, but generally show that the systematic errors were minimized for 5 µm size particles, justifying the focus on these particles in the data section.

Figure 6:
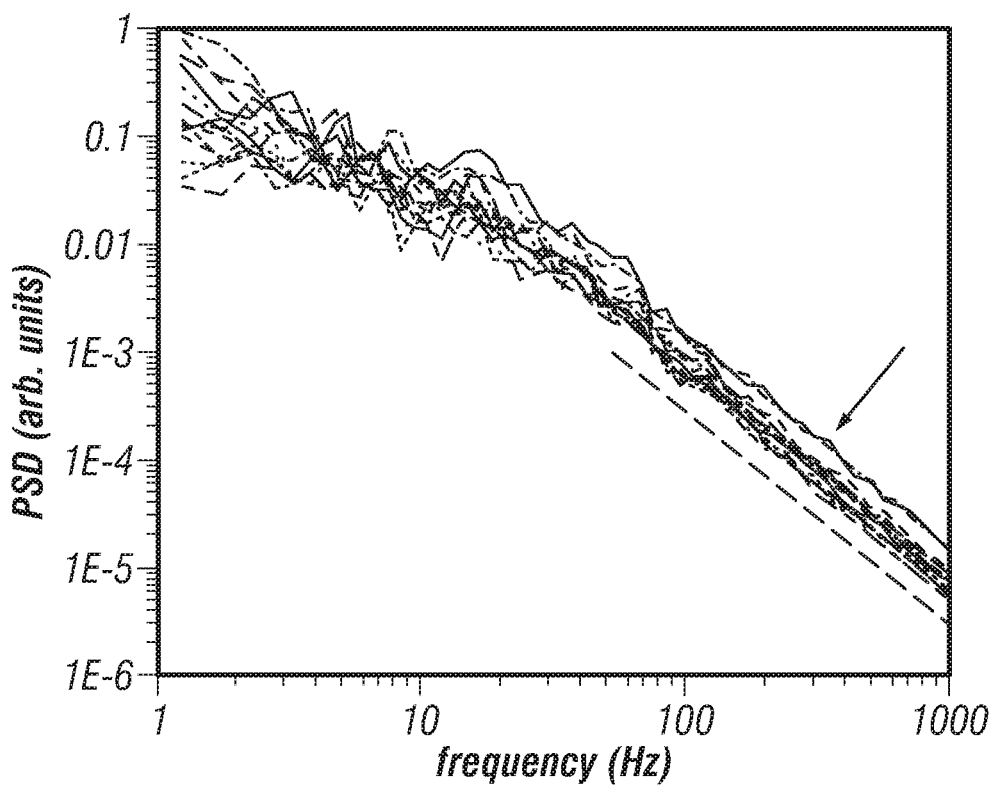
FIG. 6 presents the plot of the power spectrum of 5 μm radius particles in water at depths ranging from 10-205 μm beneath the air/water interface. The PSD with highest magnitude, indicating the highest mobility, corresponds to a particle nearest to the surface. As the particle's depth is increased, the magnitude of the power spectra decreasing monotonically converging to value consistent with a particle trapped in bulk water. The dashed black line indicates a slope of −2 expected for the high frequency part of the PSD. The black arrow denotes two spectra taken at a near-surface depth of 10 μm, which lie above all spectra taken at greater depths.

FIG. 6 provides the plot of the power spectra of the position fluctuations of 5 µm radius spheres using five sets of measurements at constant depth, each with a two second duration, and then geometrically averaged. In an ideal system, the power spectrum would be Lorentzian, but low frequency noise from the laser increased the magnitude of the power spectrum at low frequencies. Additionally, the corner frequency for the 5 µm radius particles was close to the laser noise frequency band, smearing out what would be a plateau in the power spectrum. Despite the low frequency noise, a clear trend is visible in the spectra: the spectral magnitude for the particles at the surface is significantly higher than the other particles. The arrow in FIG. 6 indicates two power spectra taken for particles positioned about two particle radii away from the surface. As the particles move away from the surface, the power spectrum decreased, converging to a depth-independent curve very similar to that measured in the bulk fluid. The increase in the power spectrum near the surface, reflecting an increase in the position fluctuations of the particle, suggests greater particle mobility. A more quantitative analysis of the particle mobility is provided herein. Data corresponding to particles at depths of ~1 particle radius or less were excluded. At such short distances to the air/water interface, the power spectrum became somewhat unreproducible, most likely due to evaporation and perhaps minor leakage of the cell. Over the course of the experiment, the water level dropped a distance comparable a particle radius. The uncertainty in the depth was estimated as ±5 µm due to these effects. Experiments done inside a closed chamber have a much smaller uncertainty in depth, about ±2 µm, since there was no detectable change in height of the surface.

Applying the methods described herein, the measurement of particles near a rigid interface was first tested. 5 µm radius particles were used and their mobility from sets of 40 measurements at each depth was calculated, by using data obtained on 5 different days. The Stokes-normalized imaginary response function (which is directly related to the mobility) was plotted as a function of depth from the glass/water interface in FIG. 7. At depths of approximately 7 particle radii, the observed mobility is experimentally indistinguishable from that of bulk water.

Figure 7:
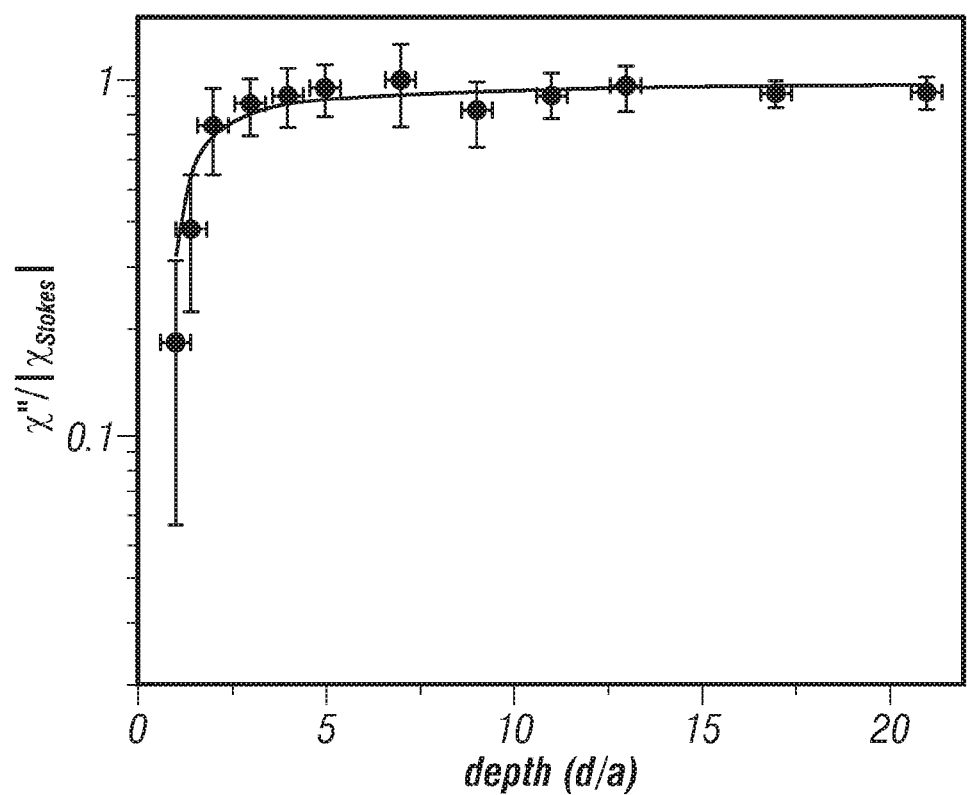
FIG. 7 presents the plot of naïvely measured imaginary response function of a particle in water as a function of distance from a glass/water interface. Theoretical values at a rigid wall are represented by a solid red line. Five sets of data were averaged together at each distance. In this experiment, the uncertainty in the depth is about ±0.4 radii.
Figure 8:
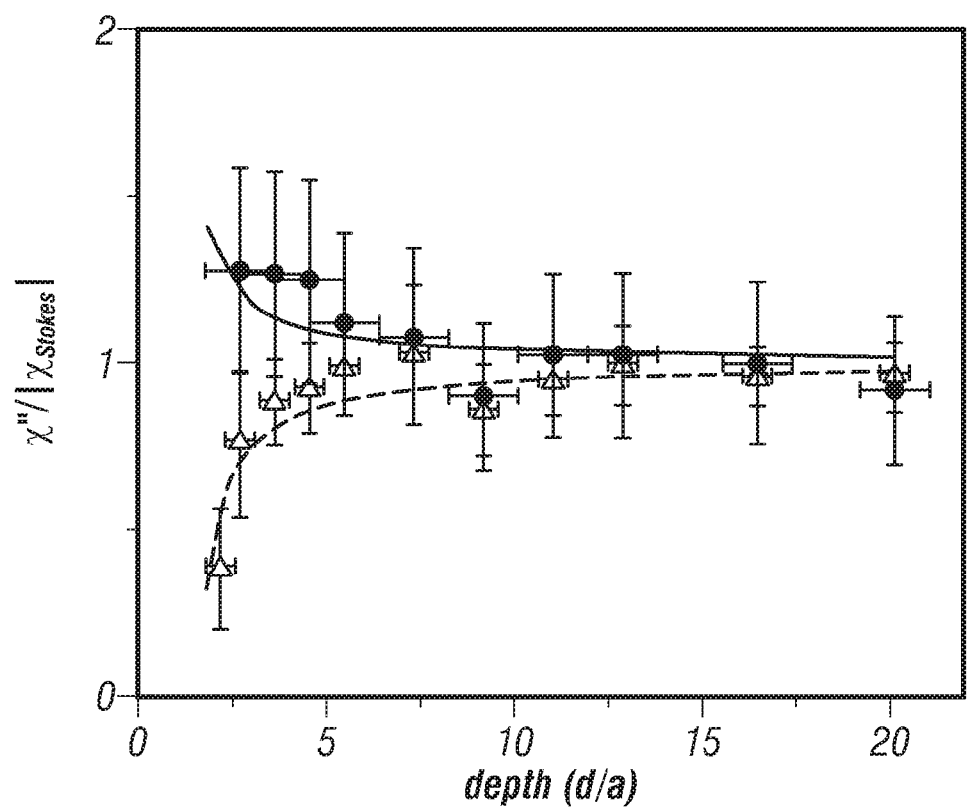
FIG. 8 presents the plot of the imaginary response function of a 5 μm radius particle in water as a function of distance from an air/water interface (blue circles) and a glass/water interface (open black triangles). The glass/water interface data follow the expected curve derived by Faxèn (dashed red line). The prediction of the imaginary response function (solid red) fits the air/water interface data well.

Results are presented in FIG. 8, can be directly compared with the data from FIG. 7 for a rigid boundary (open triangles) with the data for a free surface (solid blue circles). As predicted, the free surface exhibited an enhanced response function, corresponding to an enhanced mobility. It was found that the effect of the free surface (in agreement with theory) lead to a maximum increase of the particles' mobility by about 30% at a depth of about two particle radii. The mobility monotonically decreased to the bulk value as a function of distance from the surface. In addition, though currently at the limit of the error bars, the two sets of data are measurably different, especially when one considers the entire curve and not just a single data point. This emphasizes the trade-off between coupling with the interface (decreasing measurement sensitivity) and measuring the behavior as a function of depth (increasing measurement sensitivity). Finally, the hydrodynamic theory for the free interface theory (solid red curve) presented in paper I[35] and Faxèn's theory (dashed red curve) is plotted in FIG. 8.

The agreement of both measurements with their corresponding theories demonstrates the feasibility of probing the rheology of an interface without contacting it. The effect of a deformable and viscoelastic interface on the mobility lies between the two extremes of a free air/water surface and rigid wall. The experiments presented herein allow for the probing particle mobilities near viscoelastic interfaces in a frequency-resolved manner with sufficient precision to allow for tractable non-contact surface or interfacial rheometry for a variety of more complex and viscoelastic monolayers.

Four Quadrant Photodiode Detection.

The four quadrant photodiode detection of tracer position relies on variations of light intensity reflected back through the optical system. Unfortunately, in the submerged particle problem there were reflections both from the particle, which measure its displacement, and from the interface, which make spurious contributions to that signal. One needs to account for those spurious signals in a new way in order to make the fluctuation measurements on the submerged particles. Reflected laser light is collected by the objective and reflected onto the QPD, which had three outputs: X, Y, and SUM. The X and Y outputs are difference measurements between halves of the QPD used to establish the particle position, and the SUM output is a measure of the total intensity on the photodiode. A common issue with a laser/QPD position measurement is drift in the overall laser intensity, which can introduce systematic errors in the X and Y output. There is a standard correction which is to divide the X and Y outputs by the SUM. As a result of this normalization, changes in laser power in a standard particle trapping experiment do not significantly change the magnitude of a power spectrum generated by a times series of X or Y values.

Changes in the Background Intensity of Reflected Light as the Depth is Changed.

In the experiments presented herein, due to the index of refraction mismatch at the air/water interface, there were also strong surface reflections in addition to the reflected light from the tracer. The diffuse component of the surface reflection produced a significant signal in the SUM channel of the QPD at ~80 µm from the surface. As shown in FIG. 9, the signal was present with and without particles in the laser trap and has a strong dependence on distance from the interface. Given an incident $$\frac{A}{(d/B+1)^2}$$

laser power of A it was expected that the contribution to the SUM signal from surface reflections should vary with distance d as +C. Here B represents the focal distance and C corrects for the background illumination. These expectations were confirmed (e.g. see FIG. 7, where both the SUM signal with (dotted) and without (dashed) a particle fits to this function (red line) are shown). Because this additional signal was independent of the light reflected from the particle, it increased the value of the SUM channel but did not impact the X and Y channel signals. Therefore, if the standard normalization procedures were followed, new systematic errors would be introduced due to the surface reflection enhancement of the SUM signal.

To avoid these systematic errors, the average SUM value from the bulk depths (taking "bulk" to refer to measurement depths of 120 to 200 µm) were normalized, rather than the SUM signal measured concurrently with X and Y. Without this procedure, the data show an unphysical minimum with depth, as shown by the open symbols in FIG. 10. However, when one uses the new procedure presented herein, one obtains the results shown by the closed symbols in FIG. 10; the unphysical minimum has been eliminated. These corrected data, however, still deviate significantly from simple hydrodynamic theories particularly at small depths. The residual error is due to a particle lensing effect.

Particle Lensing Effects.

In addition to the diffusive component of surface reflections, there is a second order reflection component that enhances the variance of the X and Y signals. The surface reflected light diffracts back around the trapped particle (or refracts through it) and passes back to the objective. This particle lensing effect forms a time varying image on the QPD, causing an additional signal in the X and Y channels. This stronger signal variance in the position channels would naïvely be interpreted as a greater mobility of the particle. This is apparent in FIG. 10, where the measured values near the fixed walls disagree with the expected Faxèn's result.

In order to confirm that the systematic effects were in fact due to surface reflections, two materials with differing indices of refraction for the fixed wall were used. In this way, the same "stick" boundary conditions for the hydrodynamics were maintained, but the amount of reflected light was modulated. In FIG. 10, the apparent imaginary part of response function of a half micron radius sphere in water near either a glass wall (blue symbols) or a polycarbonate wall (green symbols) is plotted. It is clear from these data that the spurious increase in particle mobility depends on the material making up the wall, and that the more reflective polycarbonate boundary (n~1.592) generates a larger error than that of the less reflective glass (n~1.520). The dependence of the effect on the wall's refractive index demonstrates that it cannot be hydrodynamic in origin, but instead is due to the ~55% greater reflectance of the polycarbonate wall over that of the glass one.

Figure 11:
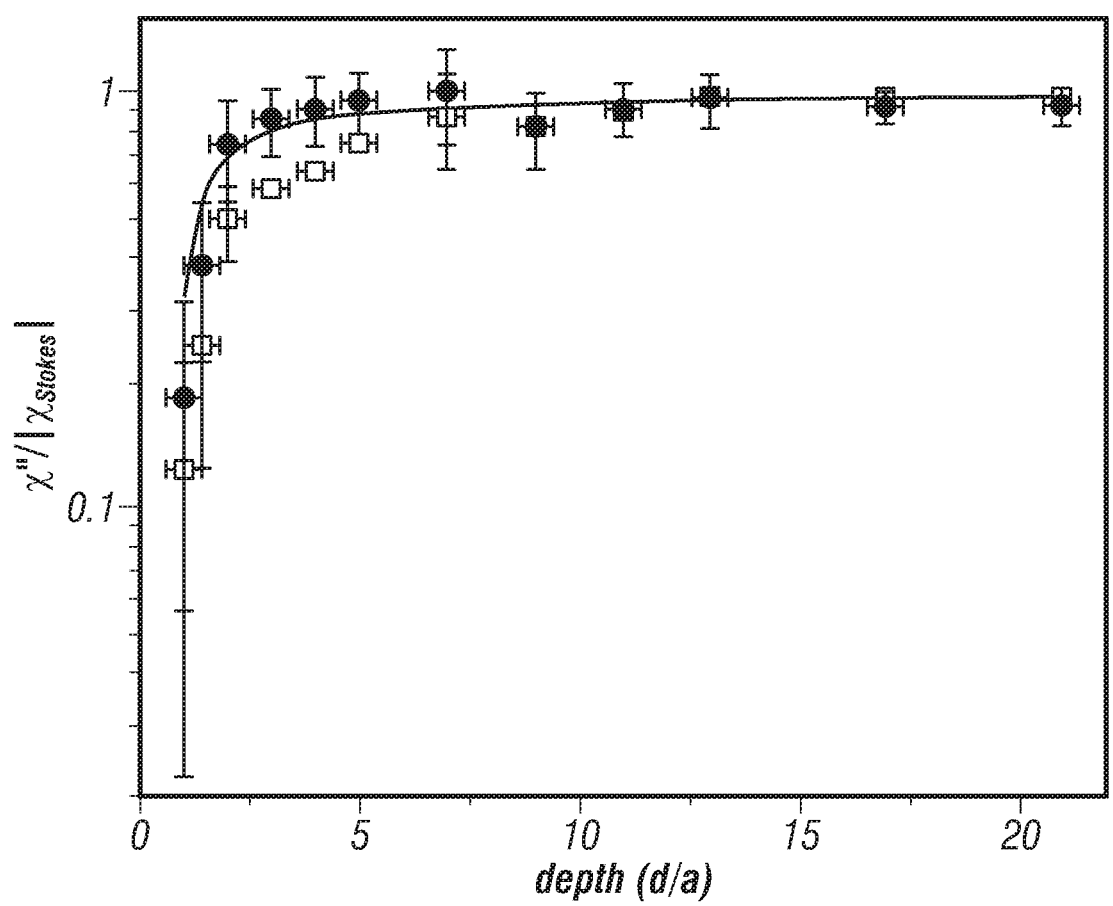
FIG. 11 presents a plot of the imaginary response function from FIG. 7 showing how results normalized by the bulk SUM signal (solid blue circles) match the theory better than the results normalized by the SUM signal at each depth (open black squares). The latter values of the response function are shown to be significantly below the theoretical curve at shallow depths. Values normalized by the bulk SUM signal closely follow the theoretical curve.

A further test of this idea was to use larger spheres to modify the lensing effect. This is illustrated in FIG. 11, where data for 5 µm particles are presented. In contrast to the half micron sphere data shown in FIG. 10, FIG. 11 demonstrates that correctly normalizing the data by the bulk SUM signal provided excellent agreement with theory, effectively eliminating the particle lensing effect. This is presumably due to the fact that the 5 micron sphere is larger than the wavelength of the laser light and thus produced less diffraction effects. The trade-off for using a larger size particle was that the amplitude of the Brownian motion becomes smaller. For the 5 µm radius tracers, their Brownian motion at frequencies above 2 kHz were not detected. The power spectra in FIG. 6 show $f^{-2}$ behavior between 200-2000 Hz as expected for a viscous fluid, but beyond this frequency, the power spectrum shows a steeper slope, which was attributed to having reached met the detection floor. As both of the systematic errors inherent in technique stem from the use of reflected light for tracer position detection, it is expected that an alternative geometry using QPD to detect the transmitted light may reduce or eliminate both problems.

Laser Tweezers Microrheology Reveals Mechanical Heterogeneities within Naturally Derived ECMs.

Figure 12A:
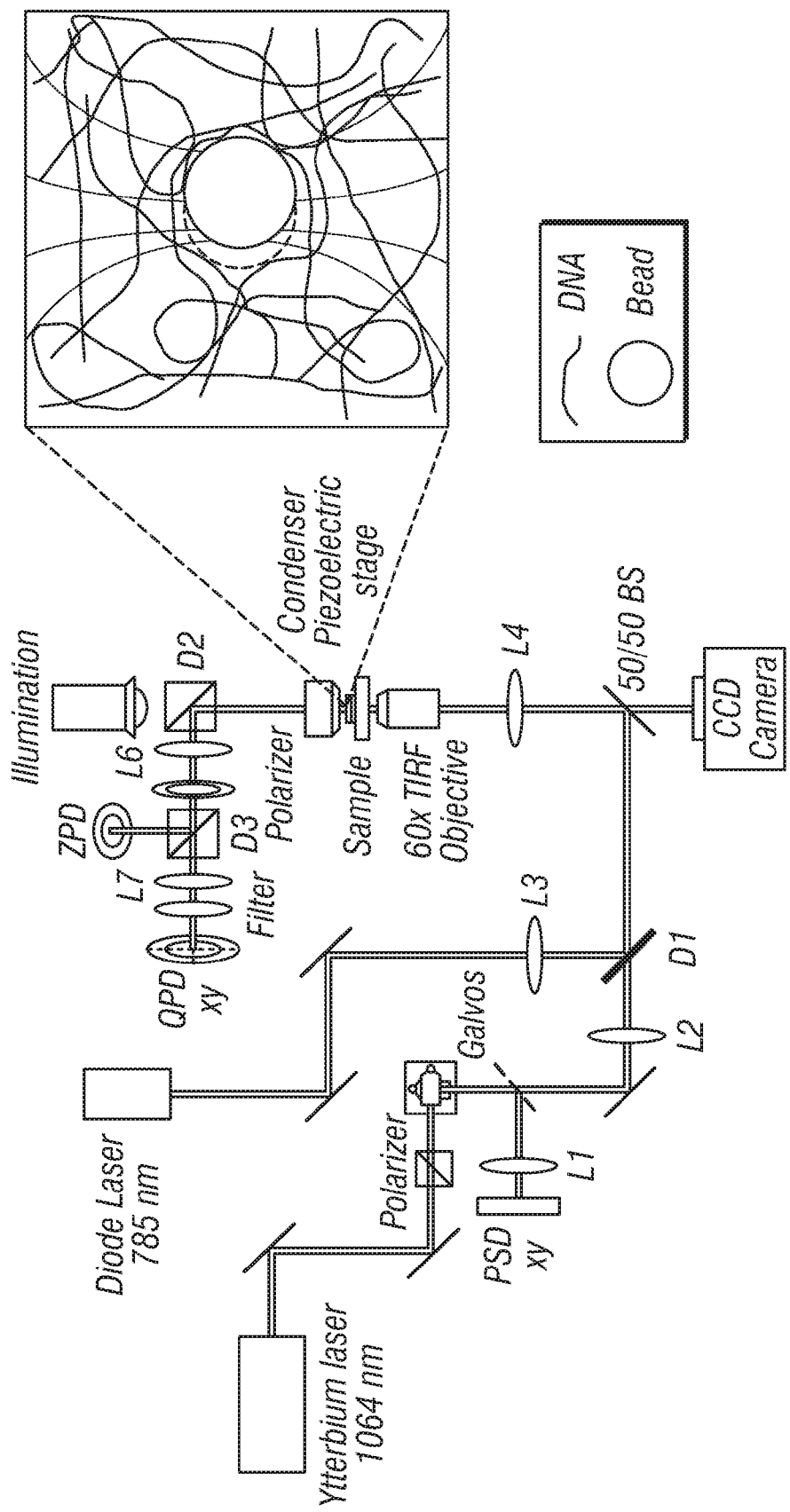
FIG. 12A-B presents a diagram of a Laser Tweezer device of the disclosure comprising microrheological methods disclosed herein that was used for the study of ECM stiffness. A microsphere is manipulated by an oscillating Ytterbium fiber-laser trapping beam. The microsphere acts as a lens to steer the diode laser detection beam as detected by the QPD. (inset) Bead motion is resisted by the ECM through elastic and viscous interactions. (B) Conceptual illustration of the proposed SPIM technique. (Left) Illustration of a cell interacting with the ECM. The ECM contains microbeads (blue circles) that are tracked or manipulated by optical tweezers (hour glass). (Right) A close-up illustration of the cell membrane-ECM interface. Standard techniques using fluctuations of beads work sufficiently far from the cell membrane.
Figure 12B:
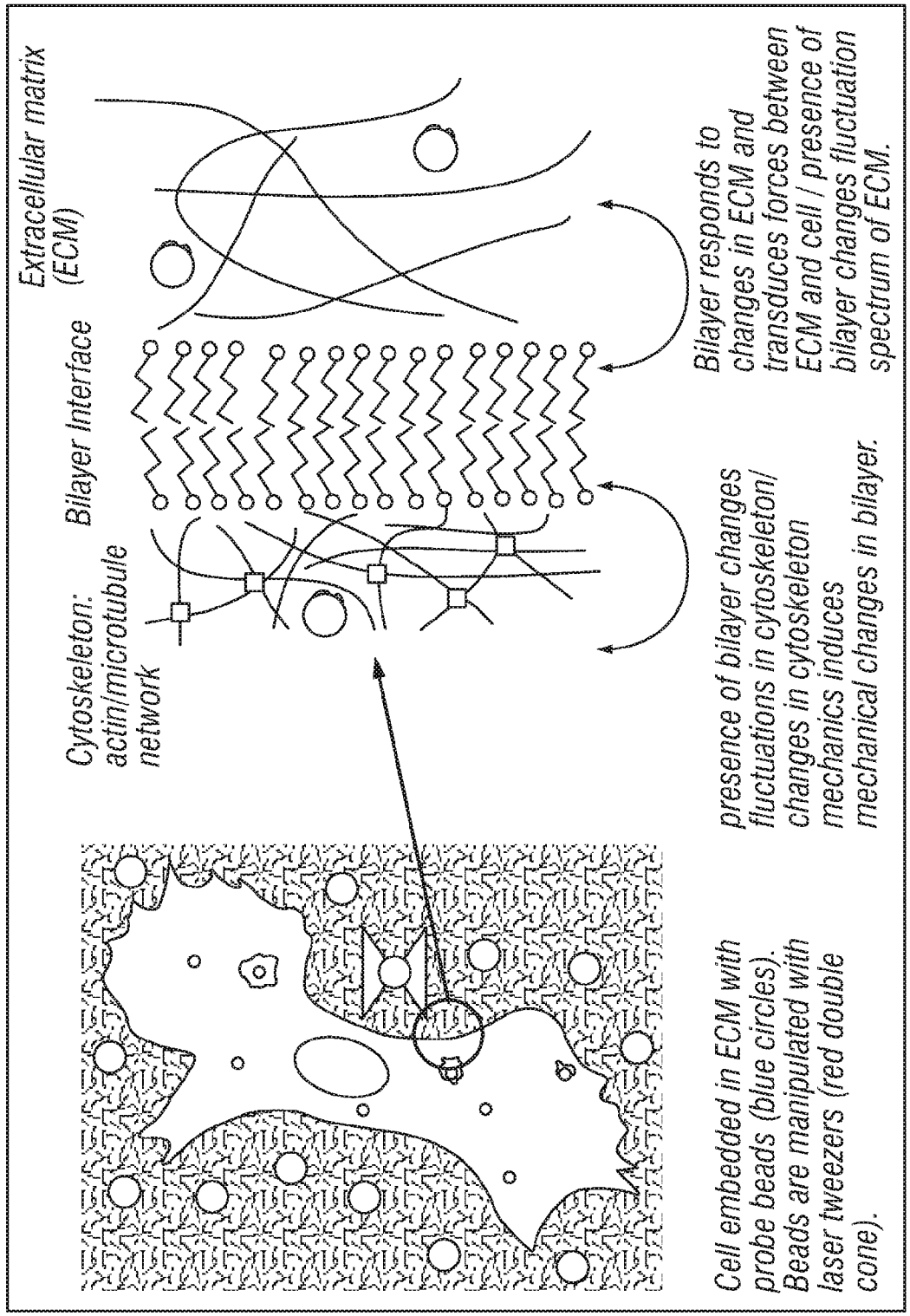

Provided herein is a device comprising microrheological methods of the disclosure, such as SPIM, that is a laser tweezers apparatus able to perform PMR and AMR (e.g., see FIG. 12). The device combines a 1064 nm trapping beam with a low power 785 nm detection beam. The beams are focused by a 60×1.45 NA objective onto a microsphere undergoing Brownian motion within a pore. The microsphere acts as a small lens that steers the detection beam as it moves throughout the pore. The deflected light is collected by the microscope condenser and imaged (in the Fourier plane) onto a quadrant photodiode ("QPD"), which outputs analog signals in proportion to the position of the laser beam on its surface. As already discussed herein, the QPD signals are used to compute the positions of the microsphere and thus reconstruct the thermally driven transverse wanderings of the microsphere. The complex shear modulus G*, which includes a measure of local stiffness, can then be calculated from the QPD signals.

Use of SPIM Methods with AMR to Study of ECM Stiffness.

As PMR underestimates the stiffness of the ECM by orders of magnitude as compared to AMR and parallel plate rheology, AMR was used for the study of ECM stiffness. AMR involves oscillating the position of the trapping beam (in this case by galvanometers (Galvos), e.g., see FIG. 12) and measuring the amplitude and phase of the probe particle's oscillation with respect to the laser trap. As with PMR, the low power detection laser is steered by the sphere and detected by the QPD. Using AMR, it was found that while parallel plate rheology estimates of G* are useful for predicting tissue-scale deformations, these estimates are blind to the heterogeneity experienced by cells, and should not substitute for local in situ measurements of stiffness. It was also observed anisotropy in ECMs, where the value of G* depended on the direction of bead oscillation. Additionally, heterogeneity surrounding the tip cell in a HUVEC model of 3D capillary morphogenesis was also observed, where the matrix was found to be stiffer near the leading edge of the cell. Importantly, AMR allowed for noncontact serial measurement of stiffness, at least 50 um below the surface of the gel, which cannot be achieved by either PMR or AFM. Given the importance and novelty of these bulk microrheological results, devices comprising microrheological methods disclosed herein, such as SPIM and S-SPIM, can lead to the discovery of similarly important aspects of interfacial mechanics in other systems.

A number of embodiments have been described herein and in Appendix A (which is incorporated herein by reference). Nevertheless, it will be understood that various modifications may be made without departing from the spirit and scope of this disclosure. Accordingly, other embodiments are within the scope of the following claims.

What is claimed is:

1. A non-contact microrheological method comprising:
    measuring fluctuation of a particle in or near a monolayer using a laser trap in combination with a back focal plane displacement detection scheme, wherein the particle is held at a fixed depth below an air/liquid, liquid/liquid, or solid/liquid interface and its fluctuations in a plane parallel to the monolayer surface is measured using a quadrant photodiode detection system, and wherein the particle is hydrodynamically coupled to the monolayer; and
    correcting the particle fluctuation measurements for changes in the background intensity of reflected light as the depth is changed, and/or for particle lensing effects acting on reflected light.

2. The non-contact microrheological method of claim 1, further comprising extracting from the particle fluctuation measurements an in-plane response function.

3. The non-contact microrheological method of claim 2, further comprising determining the in-plane response function in terms of the hydrodynamic modes of the system and their associated moduli.

4. The non-contact microrheological method of claim 2, wherein the in-plane response function takes into account the role of a subphase, the contact angle between the particle and the interface, and changes in the monolayer itself induced by the particles.

5. A device for carrying out the non-contact microrheological method of claim 1, comprising
   a monolayer trough coupled with a liquid immersion objective;
   an optical trap using a laser;
   an optical system comprising a beam expander, steering lenses, mirrors, which focuses the beam to form the optical trap, wherein the trough is attached to a stage so that the fixed objective can trap particles at various distances below the surface, wherein trapped particles scatter laser light back through the objective, onto both a quadrant photodiode ("QPD") and an intensified CCD camera, wherein the quadrant photodiode allows high frequency 2-dimensional position measurements to be recorded via a data acquisition board and analysis software and a computer for extracting particle fluctuation measurements to form an in-plane response function which takes into account the role of a subphase, the contact angle between the particle and the interface, and changes in the monolayer itself induced by the particles.

6. The device of claim 5, further comprising a laser tweezer that can measure bulk mechanical properties of biological systems.

7. The device of claim 6, wherein the device uses a response function that is measured directly by comparing an applied force and the particles displacement using an oscillatory measurement ("AMR").

8. The device of claim 6, wherein the device manipulates a particle by using an oscillating Ytterbium fiber-laser trapping beam, wherein the particle acts as a lens to steer the diode laser detection beam as detected by the QPD; and wherein the particles elastic and viscous interactions with a surrounding liquid medium can be measured.

* * * * *